United States Patent [19]

Kit et al.

[11] Patent Number: 5,128,129

[45] Date of Patent: Jul. 7, 1992

[54] INFECTIOUS BOVINE RHINOTRACHETIS VIRUS MUTANTS, VACCINES CONTAINING SAME, METHODS FOR THE PRODUCTION OF SAME AND METHODS FOR THE USE OF SAME

[75] Inventors: Malon Kit; Saul Kit; Haruki Otsuka, all of Houston, Tex.

[73] Assignees: Novagene Inc.; Baylor College of Medicine, both of Houston, Tex.

[21] Appl. No.: 591,999

[22] Filed: Oct. 1, 1990

Related U.S. Application Data

[62] Division of Ser. No. 116,197, Nov. 3, 1987, Pat. No. 4,992,051.

[51] Int. Cl.[5] .................. A61K 39/265; A61K 35/76; C12N 7/00; C12N 7/01
[52] U.S. Cl. .................................. 424/89; 435/172.1; 435/172.3; 435/235.1; 435/320.1; 935/12; 935/32
[58] Field of Search .................. 424/89, 93; 435/235.1, 435/172.3, 172.1, 320.1; 935/12, 32

[56] References Cited

U.S. PATENT DOCUMENTS 4,810,634  3/1989  Post et al. ..................... 435/235.1

FOREIGN PATENT DOCUMENTS 074808  3/1983  European Pat. Off. .

OTHER PUBLICATIONS

Van Drunen Littel-Van den Hurk et al. (1986) J. Virol 59(2), 401–410.
Zuckermann et al. (1990) J. Virol, 64(2), 802–812.
Robbins et al. (1986) J. Virol, 58(2), 339–347.
Robbins et al. (1986) J. Virol, 59(3), 635–645.

*Primary Examiner*—Robert A. Wax
*Assistant Examiner*—R. Keith Baker
*Attorney, Agent, or Firm*—Sughrue, Mion, Zinn, Macpeak & Seas

[57] ABSTRACT

Infectious bovine rhinotracheitis virus (bovine herpesvirus type 1) mutants containing deletion and/or insertion mutations in a major viral glycoprotein gene, such that no antigenic polypeptides encoded by the viral gene are produced, vaccines for infectious bovine rhinotracheitis containing the same, methods for the production of the same and methods for use of the same. Animals vaccinated with these mutants do not develop antibodies to the viral glycoprotein and can be distinguished serologically from animals infected with infectious bovine rhinotracheitis virus field strains.

58 Claims, 12 Drawing Sheets

FIG. 3

```
2
CACGCTGGTGGCCTGCGTGTGGGTCCGGCGCTGCGGCGCGGCACCGGCTGGCGGGCGCTGGCCGGGCACGTGGCCAAGGCCC

82
TGCACGCCGGCGCTGTGCTTCTGCGTCGGGGCCTGCGTGGGTCTGCGCCGACGAATGAACGGCTGCCGCCGACGGTAACGC

162
GCCTGCAGCCGCGTGTGCTCAATCCCGGACCACGAAAGCACAAACGGACGCCCTTAAAAATGTAGCCCGGCGGCGGGT

242
CGCGGCCATCTTGGATCCACCCGGCGACGCCGAGAGACCGCCAGCCCGAGACCTCGCCGCGCGTCCGCC  MET
                                                                    ATG

320
GLY PRO LEU GLY ARG ALA TRP LEU ILE ALA ALA ILE PHE ALA TRP ALA LEU LEU SER ALA
GGC CCG CTG GGG CGA GCG TGG CTG ATC GCA GCT ATT TTC GCC TGG GCG CTC CTG TCT GCC
        ApaI
380
ARG ARG GLY LEU ALA GLU GLU ALA SER PRO SER PRO PRO PRO SER PRO SER PRO
CGG CGG GGG CTC GCC GAG GAG GCG TCG GAA GCC CCC TCG CCC TCG CCT CCG CCC TCC CCA

440
THR GLU THR PRO GLU SER SER ALA GLY THR GLY ALA SER ALA PRO ARG ARG PRO THR GLY
ACC GAG ACG GAA AGC TCC GCT GGG ACC ACC GGC GCA AGC GCC CGA CGC CCA ACA GGC

500
PRO ASP ALA THR PRO GLU ASP SER THR PRO VAL LEU LEU ARG PRO LEU ARG PRO ALA PRO
CCG GAC GCT ACG CCA GAG GAC AGC ACG CCG GTG CTA CTA CGC CCG CTG CGC CCG GCG CCG

560
ARG ARG PRO CYS PRO SER THR THR THR ARG PRO LEU THR ASN SER THR PRO PRO ALA PRO
CGC CGT CCG TGT CCG AGC ACG ACG ACC CGG CTT ACC AAC AGC ACG CCG CCC GCC CCG

620
PRO GLU ASP GLY ARG PRO GLY GLY ALA GLY ASN ALA SER ARG ASP GLY ARG PRO SER GLY
CCC GAG GAC GGG CGA CCC GGC GGC GCT GGC AAC GCG AGC CGC GAT GGG CGA CCT AGC GGC
```

FIG. 3
Cont.-1

```
680
GLY GLY ARG PRO ARG PRO PRO ARG PRO SER LYS ALA PRO PRO LYS GLU ARG LYS TRP MET
GGG GGC CGG CCT CGC CCC CCG CGG CCG AGC AAA GCC CCG CCG AAG GAG CGC AAG TGG ATG

740
LEU CYS GLU ARG GLU ALA VAL ALA ALA SER TYR ALA GLU PRO LEU TYR VAL HIS CYS GLY
CTC TGC GAG CGC GAG GCC GTG GCC GCC TCG TAC GCC GAG CCG CTG TAC GTG CAC TGC GGC

800
VAL ALA ASP ASN ALA THR GLY GLY ALA ARG LEU GLU LEU TRP PHE HIS ARG VAL GLY ARG
GTG GCC GAC AAC GCC ACT GGC GGT GCG CGC CTG GAG CTC TGG TTT CAC CGC GTG GGC AGG

860
PHE ARG SER THR ARG GLY ASP ASP GLU ALA VAL ARG ASN PRO PHE PRO ARG ALA PRO PRO
TTC CGC TCC ACG CGC GGC GAC GAC GAG GCC GTG CGC AAC CCC TTT CCG CGG GCC CCG CCC
                                                                    Apol 920
VAL LEU LEU PHE VAL ALA GLN ASN GLY SER ILE ALA TYR ARG SER ALA GLU LEU GLY ASP
GTG CTG CTG TTC GTA GCC CAG AAC GGC TCG ATC GCG TAC CGT AGC GCG GAG CTG GGC GAC 980
ASN TYR ILE PHE PRO SER PRO ALA ASP PRO ARG ASN LEU PRO LEU THR VAL ARG SER LEU
AAC TAT ATT TTC CCT TCG CCC GCC GAC CCC CGC AAC TTG CCC CTG ACC GTG CGC TCC CTG
```

FIG. 3 Cont.-II

```
1040  THR ALA ALA THR GLU GLY VAL TYR THR TRP ARG ARG ASP MET GLY THR LYS SER GLN ARG
      ACG GCC GCC ACC GAG GGC GTG TAC ACT TGG CGC CGC GAC ATG GGC ACC AAG TCA CAG CGC

1100  LYS VAL VAL THR THR HIS ARG ALA PRO ALA VAL SER VAL GLU PRO GLN PRO ALA
      AAG GTC GTC ACG ACG CAC CGC GCG CCC GCT GTT TCC GTC GAA CCC CAG CCA GCG

1160  LEU GLU GLY ALA GLY TYR ALA ALA VAL CYS ARG ALA ALA ALA GLU TYR TYR PRO PRO ARG SER
      CTA GAA GGC GCC GGC TAC GCG GCG GTG TGC CGC GCC GCC GCC GAG TAC TAC CCG CCG CGC TCC

1220  THR ARG LEU HIS TRP PHE ARG ASN GLY TYR PRO VAL GLU ALA ARG HIS ALA ARG ASP VAL
      ACG CGC CTG CAC TGG TTC CGC AAC GGC TAC CCC GTG GAG GCT CGG CAC GCG CGC GAC GTC

1280  PHE THR VAL ASP ASP SER GLY LEU PHE SER ARG THR SER VAL LEU THR LEU GLU ASP ALA
      TTT ACG GTC GAC GAC TCC GGG CTC TTT TCG CGC ACG TCC GTC CTT ACG CTC GAG GAC GCG

1340  THR PRO THR ALA HIS PRO PRO ASN LEU ARG CYS ASP VAL SER TRP PHE GLN SER ALA ASN
      ACG CCA ACC GCC CAC CCG AAC CTG CGC TGC GAC GTC TCC TGG TTC CAG AGC GCT AAC

1400  MET GLU ARG ARG PHE TYR ALA ALA GLY THR PRO ALA VAL TYR ARG PRO PRO GLU LEU ARG
      ATG GAG CGC CGC TTT TAC GCG GCT GGC ACG CCG GCC GTT TAC CGC CCG CCC GAG CTG CGC

1460  VAL TYR PHE GLU GLY GLY GLU ALA VAL CYS GLU ALA ARG CYS VAL PRO GLU GLY ARG VAL
      GTG TAC TTC GAG GGC GGC GAG GCC GTC TGC GAG GCG CGC TGC GTC CCC GAG GGG CGC GTC
```

FIG. 3 Cont.-III

```
1520
SER LEU ARG TRP THR VAL ARG ASP GLY ILE ALA PRO SER ARG THR GLU GLN THR GLY VAL
TCC CTG CGC TGG ACG GTG CGC GAC GGC ATC GCC CCG TCG CGC ACT GAG CAG ACC GGC GTC

1580
CYS ALA GLU ARG PRO GLY LEU VAL ASN LEU ARG GLY VAL ARG LEU LEU SER THR THR ASP
TGC GCC GAG CGG CCC GGG CTG GTA AAC CTG CGG GTG CGC CTG CTT TCT ACA ACC GAC

1640
GLY PRO VAL ASP TYR THR CYS THR ALA THR GLY TYR PRO ALA PRO LEU PRO GLU PHE SER
GGG CCC GTC GAC TAC ACC TGC ACC GCC ACT GGC TAC CCG GCA CCG CTG CCC GAG TTC TCC
    ApaI

1700
ALA THR ALA THR TYR ASP ALA SER PRO GLY LEU ILE GLY SER PRO VAL LEU VAL SER VAL
GCG ACC GCC ACG TAC GAC GCC TCG CCC GGA CTA ATC GGA AGC CCC GTC CTC GTC AGC GTC

1760
VAL ALA VAL ALA CYS GLY LEU VAL GLY ALA VAL GLY LEU LEU LEU VAL ALA ALA SER CYS LEU
GTG GCC GTC GCC TGC GGT CTC GGG GCC GTG GGG CTC CTG GTG GCG GCC TCG TGC CTG

1820
ARG ARG LYS ALA ARG ALA ARG LEU***            GCGGGGCGGGCCCCGACGGCAAAGCCGCGCCCCCCCCCAA
CGG CGC AAG GCC CGG GCG CGC CTC TAG                            ApaI

1890
AGACCAGCCATGTACATTTCATAATAAACTAAAACAAACTTTTATTGTGTGTGTTACAGCGTTTGGGTGGGCCT

1970
TTACA
```

THE MOLECULAR WEIGHT OF THIS PROTEIN IS 54621.2

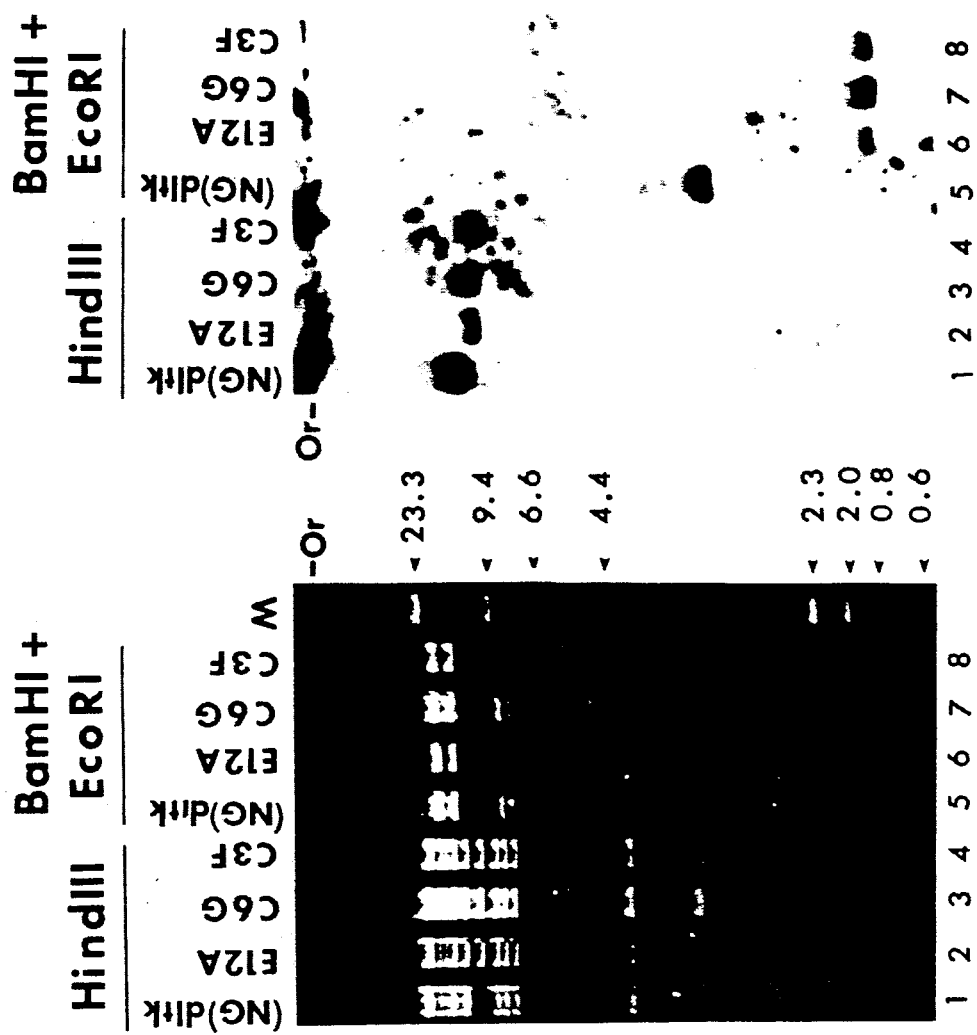

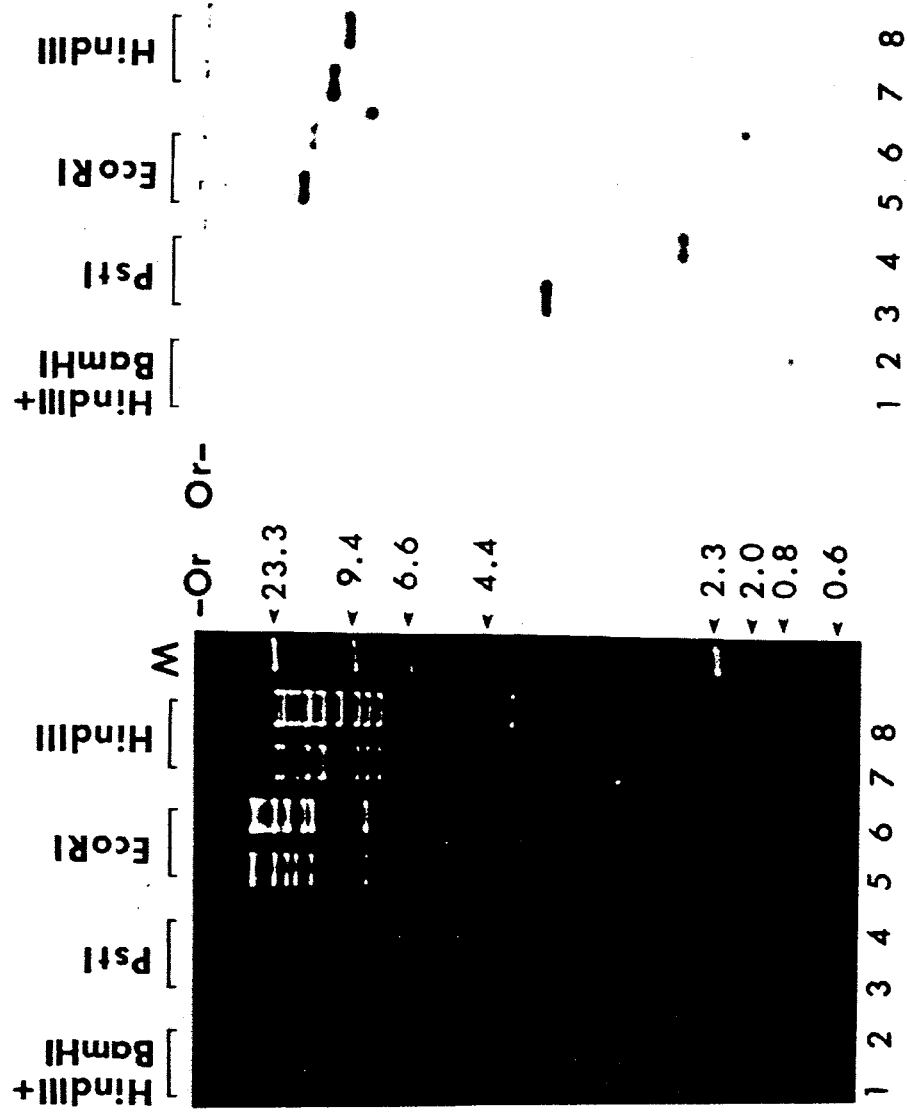

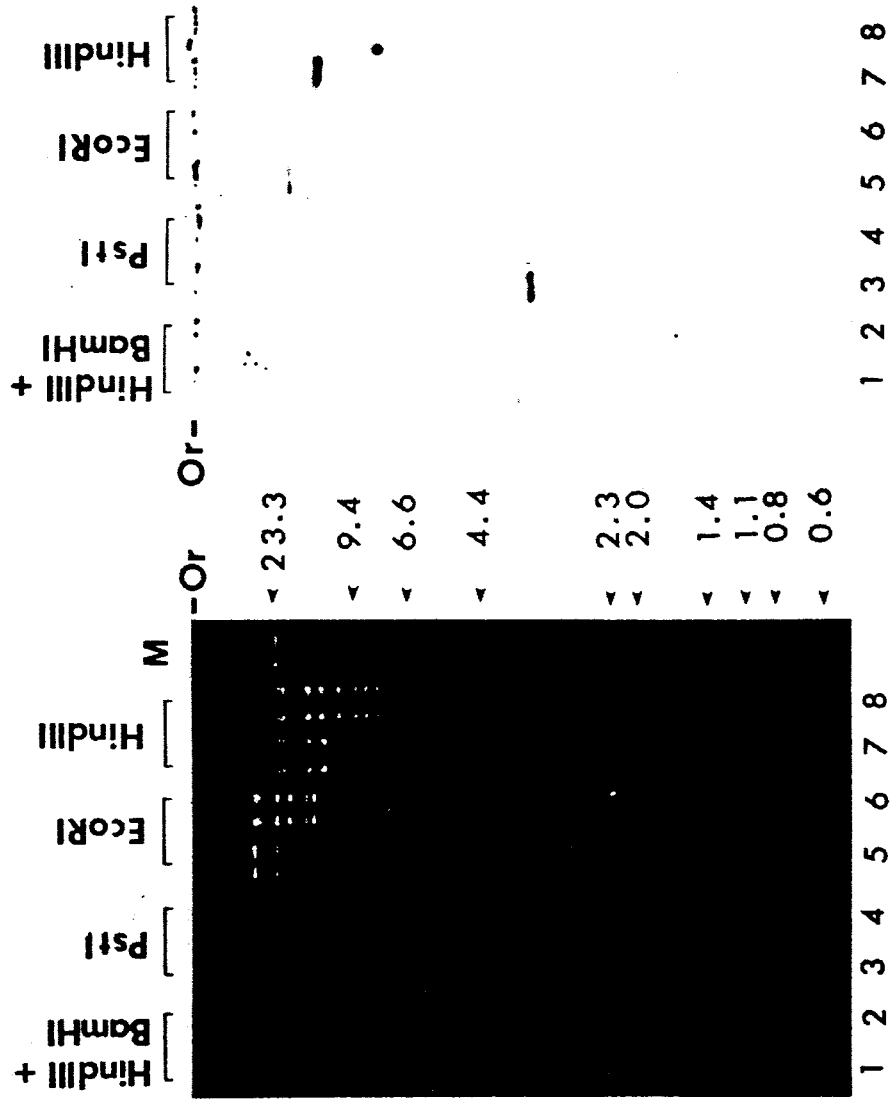

FIG. 8

| Sera | PC-14 Anti-IBRV | | | | MC2905 Anti-gIII | | | |
|---|---|---|---|---|---|---|---|---|
| IBRV Ag | Mock-Infected | Los Angeles | Cooper | (NG)dltkdlgIII | Mock-infected | Los Angeles | Cooper | (NG)dltkdlgIII |

MW (×10⁻³)

116▸
97.4▸
66▸
45▸
29▸

1  2  3  4  5  6  7  8

INFECTIOUS BOVINE RHINOTRACHETIS VIRUS MUTANTS, VACCINES CONTAINING SAME, METHODS FOR THE PRODUCTION OF SAME AND METHODS FOR THE USE OF SAME

This is a divisional of application Ser. No. 07/116,197, filed Nov. 3, 1987, now U.S. Pat. No. 4,992,051.

The invention described herein was developed during the tenure of a Research Career Award to Dr. Saul Kit from the United States Public Health Service of the Department of Health and Human Services.

FIELD OF INVENTION

The present invention relates to infectious bovine rhinotracheitis virus (bovine herpesvirus type 1) mutants containing deletion and/or insertion mutations in a major viral glycoprotein gene, such that no antigenic polypeptides encoded by the viral gene are produced. As a result, animals vaccinated with such do not develop antibodies to the viral glycoprotein and can be distinguished serologically from animals infected with infectious bovine rhinotracheitis virus field strains. The present invention also relates to vaccines for infectious bovine rhinotracheitis containing the same, methods for production of the same and methods for use of the same.

BACKGROUND OF INVENTION

I. Infectious Bovine Rhinotracheitis

Bovine herpesvirus type 1 (hereinafter "BHV-1") more commonly known as infectious bovine rhinotracheitis virus (hereinafter "IBRV"), has been associated with respiratory, reproductive, enteric, ocular, central nervous system neonatal mammary, and dermal infections of cattle (Gibbs, E. P. J. et al, *Vet. Bull,* (London), 47:317-313 (1977)). Evidence for the association of IBRV with diseases of the respiratory tract was first obtained in the early 1950's. It has since become apparent that infectious bovine rhinotracheitis (hereinafter "IBR") has a worldwide distribution. By the mid-1960's, respiratory disease caused by IBRV resulted in losses in the United States estimated at about $25 million. Additional losses associated with IBRV infections have been due to abortion storms, dramatic losses in milk yield, metritis, enteritis, and meningitis, Since 1972, more severe forms of IBRV respiratory infections have become widespread in Canada and Western Europe. New IBR outbreaks probably result from exposure to imported asymptomatic IBRV carriers or exposure to infected animals prior to the onset of clinical disease. Hence, the importation of IBRV-infected livestock may be restricted or forbidden by some countries.

The spread of IBR in naturally and artificially bred cattle also poses a serious problem, especially with the continued, widespread use of frozen semen. In addition, recurrent shedding of IBRV from infected bulls constitutes a significant threat to the artificial insemination industry in the United States and to the worldwide distribution of bovine germ plasm. The incrimination of IBRV as the etiologic agent of oophoritis and salpingitis with resultant infertility and sterility adds to the seriousness of IBRV infections.

Natural IBRV infections of species other than cattle occur in swine, goats, water buffalo, wildebeasts, ferrets, and mink. Experimental infections have been established in swine, goats, mule deer, ferrets and rabbits (Joo, H. S. et al. *Am. J. Vet. Med. Assoc.,* 45:1924-1927 (1984)).

The severity of illness resulting from IBRV infections depends upon the virus strain and on the age of the animal affected. After recovery from infection, animals may show clinical signs of recurrent disease without being reexposed to the virus. Recurrent disease without reexposure occurs because the virus remains dormant i e., latent, in neurons of the sensory ganglia of its host and can be reactivated, even after long periods (Rock, D. L. et al. *J. Gen. Virol.,* 67:2515-2520 (1986)). Dexamethasone treatment can also provoke nasal shedding of the virus with or without clinical symptoms of active IBR. This suggests that reactivation and release from neuronal sites and, possible, persistent infection of other tissues can occur (Rossi, C. R. et al. *Am. J. Vet. Res.,* 43:1440-1442 (1982)). Reactivation of IBRV from latency and symptomatic shedding can also occur spontaneously so that cattle latently infected with field strains of IBRV represent a sporadic source of virus transmission and herd infection.

II. Known IBR Vaccines

Control of IBR is based largely on vaccination. Currently, three types of IBR vaccines are being employed: (1) killed virus vaccines: (2) subunit vaccines;and (3) modified-live virus (hereinafter "MLV") vaccines (U.S Pat. Nos. 3,634,587; 3,925,544; and 4,291,019). Killed IBR vaccines are produced by treating the virus with chemicals, such as formalin or ethanol, and/or physical agents, such as heat or ultraviolet irradiation Subunit IBR vaccines are prepared by solubilizing IBRV-infected cell cultures with nonionic detergents and purifying some of the solubilized virus proteins (Babiuk, L. A. et al. *Virol.,* 159:57-66 (1987)). Early MLV vaccines were designed for parenteral administration consisted of IBRV attenuated by rapid passage in bovine cell cultures. More recently, parenterally administered MLV vaccines have been attenuated by adaptation of IBRV to porcine or canine cell cultures, by adaptation to growth in cell culture at a low temperature (30° C.) or by selection of heat-stable virus particles (56° C. for 40 min). Specialized types of MLV vaccines are those administered intranasally. These MLV vaccines are attenuated by serial passage in rabbit cell cultures or by treatment of IBRV with nitrous acid followed by selection for temperature-sensitive mutants. A temperature-sensitive virus is one that replicates efficiently at 32° C. to 38° C., but not at about 39° C. to 41° C. (Todd, J. D. et al. *J. Am. Vet. Med. Assoc.,* 159:1370-1374 (1971); Kahrs, R. F. et al. *J. Am. Vet. Med. Assoc.,* 163:437-441 (1973); Smith, M. W. et al, *Can. Vet. J.,* 19:63-71 (1978); Zygraich, N. et al, *Res. Vet. Sci.,* 16:328-335 (1974); and U.S. Pat. Nos. 3,907,986 and 4,132,775).

The currently available IBR vaccines discussed above have serious disadvantages and have, therefore, proved unsatisfactory in commercial use. More specifically, although killed IBR vaccines are considered by some to be safer than MLV vaccines, i.e., they cannot establish latency and they eliminate the problem of postvaccination shedding, they are expensive to produce, must be administered several times, and disadvantageously require adjuvants. In addition, with their use, there is the possibility of fatal hypersensitivity reactions and nonfatal urticaria. Further, some infectious virus particles may survive the killing process and thus cause disease. Moreover, cattle vaccinated with killed IBR vaccines can be infected at a later time with virulent virus and can shed virulent virus, thereby spreading infection in the herd (Frerichs, G. N. et al. *Vet. Rec.,* 111:116-122 (1982); and Wiseman, A. et al. *Vet. Rec.,* 104:535-536 (1979)). Thus, although killed IBR vaccines can provide some protection against IBR, they are generally inferior to MLV vaccines in providing long-term protection.

Subunit vaccines are often less toxic than killed virus vaccines, and may induce novel immunologic effects which can be of significant value. The technique for subunit vaccine preparation involves removal of capsid proteins, while leaving intact antigenic proteins that elicit protective immunity. This creates a potential for the development of serologic procedures to differentiate vaccinated from naturally infected animals. Further, subunit vaccines, though antigenic, do not contain live virus and, thus, cannot be transmitted to other animals, cause abortion, or establish latency (Lupton, H. W. et al. *Am. J. Vet. Res.,* 41:383-390 (1980); and le Q. Darcel, C. et al. *Can. J. Comp. Med.,* 45:87-91 (1981)). However, subunit vaccines, like killed vaccines, do not generally prevent infection and latency when cattle are subsequently exposed to virulent IBRV field strains. Other disadvantages of subunit vaccines are the high cost of purification and the requirement of several injections with adjuvant.

MLV IBR vaccines have the important advantage that they produce rapid protection and activate cell-mediated and humoral components of the immune system. In the case of intranasal vaccination, localized immune responses that suppress later replication of virulent IBRV in the respiratory tract contribute significantly to protection. The local immune responses include production of interferon and antibodies in nasal secretions (Kucera, C. J. et al, *Am. J. Vet. Res.,* 39:607-610 (1978)). Extensive utilization of MLV IBR vaccines has reduced the frequency of occurrence of IBR. However, most of the available MLV IBR vaccines are not entirely satisfactory. More specifically, there is concern as to their safety, especially if the vaccine virus itself produces latency and may be shed and transmitted to susceptible cattle.

Maximal utilization of intramuscularly (hereinafter "IM") administered MLV IBR vaccines has been especially hampered by the hazards of vaccine-induced abortions. That is, abortion rates as high as 60% have been reported after IM injection of some MLV IBR vaccines (Kahrs, R. F., *J. Am. Vet. Med. Assoc.,* 171:1055-1064 (1977); and Kendrick, J. W. et al. *Am. J. Vet. Res.,* 28:1269-1282 (1967)). In addition, with the MLV IBR vaccines currently in use, there is the danger of reversion to virulence.

In a search for safer MLV IBR vaccines, specialized vaccines have been developed (Todd, J. D. et al. *J. Am. Vet. Med. Assoc.,* 159:1370-1374 (1971); Kahrs, R. F. et al. *J. Am. Vet. Med. Assoc.,* 163:427-441 (1973); Smith, M. W. et al. *Can. Vet. J.,* 19:63-71 (1979); Zygraich, N. et al. *Res. Vet. Sci.,* 16:328-335 (1974); and Kucera, C. J. et al. *Am. J. Vet. Res.,* 39:607-610 (1978)). These vaccines have been found to be immunogenic and safe for intranasal (hereinafter "IN") inoculation to pregnant cattle and can prevent abortions in pregnant cows which have been challenge-exposed to virulent IBRV. However, they have a disadvantage in that they can only be administered by the IN route. This is because, when administered IN, one such IBR vaccine replicates to a limited extent at the lower temperature of the upper respiratory tract. However, when administered IM, the vaccine replicates poorly or not at all at normal body temperature (Zygraich, N. et al. *Res. Vet. Sci.,* 16:328-335 (1974)). On the other hand, another IBR vaccine is insufficiently attenuated for IM administration to pregnant animals although safe when given IN (Todd, J. D., *J. Am. Vet. Med. Assoc.,* 163:427-441 (1973)). Furthermore, some of the vaccine strains produce mild or moderate respiratory disease even after IN administration, and they do not prevent signs of IBR following field challenge exposure (Kahrs, R. F. et al. *J. Am. Vet. Med. Assoc.,* 163:437-441 (1973)).

Accordingly, neither the IM-administered MLV IBR vaccines, which are unsafe for pregnant cows, nor the MLV IBR vaccines that must be administered IN, discussed above fit comfortably into many of the current management practices. That is, vaccination of large numbers of cattle by the IN route is inconvenient and potentially dangerous to animal handlers. In addition, screening to identify pregnant animals prior to immunization is often not desirable or cost effective.

III. Attenuated Properties of Thymidine Kinase-Negative Herpesvirus Mutants

Recently, temperature-resistant, thymidine kinase negative (hereinafter "tk$^-$") IBR vaccines derived from the thymidine kinase positive (hereinafter "tk$^+$"), i.e., wild-type, Los Angeles strain of IBRV (ATCC No. VR-188) have been developed which overcome many of the problems that have limited the use of currently available vaccines (Kit, S. et al. *Virol.,* 130:381-389 (1983); Kit, S. et al. *Arch. Virol.,* 86:63-83 (1985); Kit, S. et al, *Vaccine,* 4 55-61 (1986); and U.S. Pat. Nos. 4,569,840 and 4,703,011, which articles and patents are incorporated by reference herein in their entirety). These IBR vaccines consist of plaque-purified IBRV isolates that replicate equally well at either 39.1° C. or 34.5° C. in rabbit skin and bovine tracheal cells. Hence, they are designated "temperature-resistant". This is in contrast to those IBRV strains that are designated, "temperature-sensitive", that is, those used for the IN-administered vaccines, which replicate only about $10^{-3}$ to $10^{-7}$ as well at 39.1° C. as at 34.5° C. In addition to the ability to replicate equally well at 39.1° C. or 34.5° C., the tk$^-$ IBR vaccines lack the ability to produce a functional thymidine kinase enzyme (hereinafter "TK") in infected cells. In one vaccine, designated IBRV(B8-D53) (ATCC No. VR-2066) (U.S. Pat. No. 4,569,840), the failure to produce a functional TK results from a mutagen-induced mutation. With a second vaccine, designated IBRV(NG)dltk (ATCC No. VR-2112) (U.S. Pat. No. 4,703,011), the failure to produce a functional TK results from a deletion of about 400 base pairs (hereinafter "bp") from the coding sequences of the IBRV tk gene as well as the insertion, into the IBRV tk gene, of a 40 bp oligonucleotide with stop codons in all three reading frames. The two characteristics, i.e., temperature resistance and tk$^-$, directly contribute to the superiority of these mutant IBRVs as vaccines.

While the temperature-resistance and tk$^-$ characteristics of the IBRV mutants discussed above greatly improve their safety and usefulness of vaccines, the dormancy feature of IBRV makes it difficult to effect eradication of IBR through the application of quarantine measures which are intended to prevent the spread of IBR by the isolation of IBRV-infected herds and the slaughter of IBRV-infected animals. That is, with existing MLV IBR vaccines, it is difficult to determine whether a specific animal, which does not show symptoms of illness, is a carrier of a dormant IBRV, since usage of most current vaccines masks infections. Hence, since animals which appear healthy may actually be carriers and, thus, spreaders of IBRV, it is important to be able, even after vaccination, to identify infected animals and herds so as to be able to apply quarantine measures. Embodiments of the present invention were developed to meet this need.

In addition, some countries require that imported livestock, whether for breeding, for stocking of farms, or for market, be tested and shown not to be carriers of IBRV, i.e., the animals cannot be imported unless they are seronegative for IBRV, With current killed and MLV IBR vaccines, a producer who elects to protect his animals from the diseases which accompany the stresses of shipping, or who is forced by the circumstances of IBRV infection in an endemic region to vaccinate susceptible animals, finds himself at a severe economic disadvantage, since vaccination of the stock will result in a positive serological test for IBRV. Revaccination to enhance protection will further increase IBRV antibody titers. As a result, the farmer's ability to export valuable livestock and to sell his stock at home is restricted and he is at a disadvantage whether he vaccinates or does not vaccinate. An IBR vaccine that can safely be administered, protects cattle from disease and dormant infections caused by field strains of IBRV, has a low or non-existent probability of reversion to virulence and, yet, does not produce a positive serological test for IBRV would allow exportation of livestock and vaccination programs to be pursued unhindered by the fear of quarantine. Such a producer could then minimize losses within his own herd, while animal health authorities could continue with their respective control measures. Embodiments of the present invention were also developed in order to meet these needs.

IV. The Genomes of IBRV

The genomes of IBRV strains consist of linear, double-stranded, noncircularly permuted DNA molecules, approximately 135-140 kilobases (hereinafter "kb") in size. Analyses of the genomes of IBRV by electron microscopy and with restriction nuclease enzymes have shown that they consist of a sequence of DNA, designated as the short unique (hereinafter "$U_S$") sequence, about 13 kb in size. The $U_S$ sequence is bracketed by inverted repeat and terminal repeat sequences (hereinafter "$IR_S$" and "$TR_S$," respectively), each about 11.5 kb in size. Another unique sequence, i.e., the long unique (hereinafter "$U_L$") sequence, which is about 100 kb in size, comprises the remainder of the DNA molecule (Hammerschmidt, W. et al. *J. Virol.*, 58:43-49 (1986); Engels, M. et al. *Virus Res.*, 6:57-73 (1986/87); and Mayfield, J. E. et al. *J. Virol.*, 47:259-264 (1983)). This genome structure exemplifies a Class D herpesvirus and is also found in pseudorabies virus (hereinafter "PRV"), equine herpesvirus types 1 and 3, and varicella-zoster virus. A consequence of such a genome structure is the ability to invert $U_S$ relative to $U_L$ leading to two isomeric structures of the DNA molecule. Physical maps of the genomes of several IBRV strains have been established for restriction endonucleases HindIII, BamHI, HpaI, EcoRI, and BstEII. Specific differences in the restriction endonuclease patterns of IBRV strains have been reported. Analyses of the restriction endonuclease patterns of the DNAs of more than 100 IBRV strains has allowed three different groups to be distinguished, but these do not correlate with epidemiological features (Engels, M. et al. *Virus Res.*, 6:57-73 (1986/1987)).

Although IBRV encodes 50 to 100 genes, few of the viral genes have been located on the physical map of the IBRV genome. The IBRV tk gene is located within the HindIII-A restriction fragment at about 0.47 map units as shown in FIG. 1 (also see FIG. 1 of U.S. Pat. No. 4,703,011). The IBRV gene encoding glycoprotein gI has also been mapped in the HindIII-A fragment, to the left of the IBRV tk gene, at approximately map units 0.405 to 0.432 (Lawrence, W. C. et al. *J. Virol.*, 60:405-414 (1986)).

One aspect of the present invention entails identification of the map location of another IBRV glycoprotein gene, that is, IBRV gIII. The data presented herein shows that the IBRV gIII gene maps at about 0.11 to 0.12 map units in the HindIII-I and BamHI-E fragments of IBRV (see FIG. 1).

V. IBRV Glycoproteins

Like most herpesviruses studied to date, IBRV specifies more than 25 structural polypeptides (Misra, V. et al. *J. Virol.*, 40:367-378 (1981); and Van Drunen-en Littel-van den Hurk, S. et al. *J. Virol.*, 59:401-410 (1986)). Among these polypeptides, to date, 10 or more glycosylated species have been identified. The virus-specific glycoproteins have a pivotal role in host-virus relationships since they are incorporated into the plasma membrane of the host cell, and ultimately become constituents of the virion envelope. In the latter capacity, they have important roles in recognition, attachment, and penetration of the virus into susceptible cells, in syncytia formation, and in different responses of the bovine immune system to IBRV infection, such as virus neutralization and the immune destruction of infected cells.

Recent immunoprecipitation experiments with monospecific antisera and monoclonal antibodies have shown that the following three sets of coprecipitating glycoproteins; (1) 180 and 97 Kilodaltons (hereinafter "kD") molecular weight glycoproteins; (2) 150 kD and 77 kD molecular weight glycoproteins; and (3) 130 kD, 74 kD and 55 kD molecular weight glycoproteins; are the major components of the IBRV envelope (Marshall, R. L. et al. *J. Virol.*, 57:745-753 (1986)). These glycoproteins are also found on the surface of IBRV-infected cells and react with neutralizing monospecific antisera and monoclonal antibodies. Analyses under nonreducing conditions have shown that the 74 kD and 55 kD molecular weight glycoproteins interact through disulfide bonds to form the 130 kD molecular weight glycoprotein, designated IBRV gI (Van Drunen Littel-van den Hurk, S. et al. *J. Virol.*, 59:401-410 (1986)). Partial proteolysis studies have also shown that the 180 kD molecular weight glycoprotein is a dimeric form of the 97 kD molecular weight glycoprotein, designated IBRV gIII, and that the 150 kD molecular weight glycoprotein is a dimer of the 77 kD molecular weight glycoprotein, designated IBRV gIV, but that these dimers are not linked by disulfide bonds.

In addition, minor glycoproteins of about 115 kD, 64 kD, and 45 kD molecular weight, and a non-glycosylated protein of about 107 kD molecular weight are removed from purified IBRV particles by detergent treatment. The 115 kD molecular weight glycoprotein, designated IBRV gII, appears to be virus-specific, since it is precipitated by monoclonal antibodies to IBRV. However, the 64 kD and 45 kD molecular weight glycoproteins are not precipitated by anti-IBRV convalescent antisera. Antisera to the 64 kD molecular weight glycoprotein precipitates several polypeptides from uninfected cell lysates, suggesting that the 64 kD molecular weight glycoprotein and, perhaps, the 45 kD molecular weight glycoprotein are proteins of cellular origin associated with the IBRV virion envelope.

Antigenically distinct precursors to each of the IBRV glycoproteins or glycoprotein complexes have been identified by monoclonal antibodies. The precursors for IBRV gI have molecular weights of about 117 kD and 62 kD. The precursors for IBRV gII, IBRV gIII and IBRV gIV have molecular weights of about 100 kD, 69 kD and 63 kD, respectively. These precursors are sensitive to endo-$\beta$-N-acetylglucosaminidase H treatment, indicating that they represent partially glycosylated, high mannose-type intermediate forms generated by cotranslational glycosylation of the primary, unglycosylated precursors of IBRV gI, IBRV gII, IBRV gIII and IBRV gIV, which had apparent molecular weights of about 105 kD, 90 kD, 61 kD and 58 kD, respectively (Van Drunen Littel-van den Hurk, S., et al. *J. Virol.*, 59:401–410 (1986)).

It is now recognized that in herpesviruses, more than one glycoprotein elicits virus-neutralizing antibodies and cytotoxic lymphocytes which aid in preventing infection and in recovery from infection. For example, monospecific antisera against each of the herpes simplex virus type 1 (hereinafter "HSV-1") glycoproteins, gB gC, gD, and gE, is able to neutralize virus and mediate complement-dependent cytolysis of virus-infected cells (Norrild, B. et al, *J. Virol.*, 32:741–748 (1979)). Similarly, monoclonal antibodies against glycoproteins gB, gC, gD, and gF of herpes simplex virus type 2 (hereinafter "HSV-2") mediate immune lysis (Balachandran, N. et al. *Infect. Immun.*, 37:1132–1137 (1982)). In addition, neutralizing antibodies are produced against each of the PRV glycoproteins gII, g92, and gp50. Further, passive immunization of animals with monoclonal antibodies directed against either PRV gp50 or PRV g92 protects them from wild-type infections (Hampl, H. et al. *J. Virol.*, 52:583–590 (1984); Ben Porat, T. et al. *Virol.*, 154:325–334 (1986); and Wathen, L. M. K. et al. *Virus Res.*, 4:19–29 (1985)). With regard to IBRV major glycoproteins, gI, gIII and gIV, induce high levels of neutralizing antibodies in cattle and participate in antibody-dependent cell cytotoxicity (Babiuk, L. A. et al. *Virol.*, 159:57–66 (1987)).

To develop a vaccine with a serological marker that distinguishes vaccinated animals from animals infected with field strains, it was necessary in the present invention to identify an IBRV glycoprotein gene which is nonessential for virus replication.

The IBRV gI glycoprotein appears to correspond to the HSV-1 gB glycoprotein (Laurence, W. C. et al, *J. Virol.*, 60:405–414 (1986)) and the PRV gII glycoprotein (Mettenleiter, T. C. et al. *Virol.*, 152:66–75 (1986)). Further, the PRV gII glycoprotein like the IBRV gI glycoprotein, consists of about 70 kD and 58 kD molecular weight polypeptides covalently linked via disulfide bonds. In addition, the PRV gII glycoprotein shares 50% amino acid homology with the aligned HSV-1 gB glycoprotein and monospecific antisera made against the PRV gII glycoprotein immunoprecipitates the HSV-1 gB glycoprotein from infected cells (Robbins, A. K. et al, *J. Virol.*, 61:2691–2701 (1987)). However, there is a great deal of data indicating that the HSV-1 gB gene and PRV gII gene are essential for virus replication (Spear, P. G., In: The Heroesviruses, 3:315–356 (1985); Marlin, S. D. et al. *J. Virol.*, 3:128–136 (1985); Lawrence, W. C. et al. *J. Virol.*, 60:405–414 (1986); and Bzik, D. J. et al. *Virol.*, 137:185–190 (1984)). Thus, the IBRV gene encoding the corresponding IBRV glycoprotein, i.e., IBRV gI, does not appear to be a promising candidate as an IBRV serological marker.

Viable HSV-1 and HSV-2 mutants which fail to express the gC glycoprotein have been isolated (Holland, T. C. et al. *J. Virol.*, 52:566–574 (1984); Draper, K. G. et al. *J. Virol.*, 51:578–585 (1984); Homa, F. L. et al. *J. Virol.*, 58:281–289 (1986); and Johnson, D. C. et al. *J. Virol.*, 58:36–42 (1986)). Similarly, a PRV mutant, PRV(dlg92/dltk), with a deletion in the PRV g92 gene has been isolated (Kit, S. et al. *Am. J. Vet. Res.*, 48:780–793 (1987); and U.S. patent application Ser. No. 823,439, filed Jan. 28, 1986). PRV(dlg92/dltk) does not express a functional TK or antigenic PRV g92 polypeptides, but replicates to titers of over $10^8$ p.f.u./ml in rabbit skin and swine testicle cells. Further, extracts from cells infected with PRV(dlg92/dltk) do not contain a protein precipitated by anti-g92 monoclonal antibodies and pigs vaccinated with PRV(dlg92/dltk) do not produce antibodies to PRV g92 polypeptides, but do produce antibodies to other polypeptides. In addition, safety and efficacy studies have demonstrated that PRV(dlg92/dltk) elicits an immune response in pigs and mice and protects them from lethal doses of virulent challenge strains of PRV (Kit, S. et al, "Genetically Engineered Pseudorabies Virus Vaccine With Deletions in Thymidine Kinase and Glycoprotein Genes," Vaccines 87, pages 345–349, Cold Spring Harbor Lab., Cold Spring Harbor, N.Y. (1987)). Deletion of the PRV g92 gene does not reduce the ability of PRV(dlg92/dltk) to generate a protective immune response or virus-neutralizing antibody in swine or mice. However, because of the PRV g92 deletion, animals immunized with PRV(dlg92/dltk) can be distinguished serologically from those infected with field strains of PRV. Hence, PRV(dlg92/dltk) exemplifies a safe and efficacious vaccine (U.S. patent application Ser. No. 823,439, filed Jan. 28, 1986). Thus, it was postulated in the present invention, that a better candidate for a dispensable IBRV glycoprotein marker gene might be the IBRV gene which corresponds to the HSV gC gene and the PRV g92 gene.

Other glycoprotein genes which are nonessential for IBRV replication in cultured cells might also be useful as IBRV serological markers. Nonessential IBRV glycoprotein genes are probably located in the $U_S$ segment of the IBRV genome since the HSV-1 glycoprotein genes gE ($U_S8$), gG ($U_S4$), and gI ($U_S7$) map in the $U_S$ portion of the HSV-1 genome, and they are "dispensable" for virus replication, at least in some cell lines in tissue culture (Longnecker, R. et al, *Science*, 236:573–576 (1987)); and PRV glycoprotein genes, gI, gp63, and gX, are located in the $U_S$ segment of the PRV genome and they are also "dispensable" for virus replication in cultured cells (Petrovskis, E. A. et al. *J. Virol.*, 60:1166–1169 (1986); Petrovskis, E. A. et al, *Virol.*, 159:193–195 (1987) Mettenleiter, T. C. et al. *J. Virol*, 61:2764–2769 (1987); and Thomsen, D. R. et al. *J. Virol.*, 61:229–232 (1987)).

In the present invention, it has been possible for the first time to identify and map the location, and to clone and sequence the IBRV gIII gene. Further, in the present invention, it has been first determined that the IBRV gIII gene is dispensable for virus replication in cultured cells. As a result, it has been possible for the first time in the present invention to genetically engineer mutations in the IBRV gIII gene so as to provide IBRVs wherein animals vaccinated with such, due to a deletion and/or insertion mutations in the IBRV gIII gene, fail to produce any antigenic polypeptides encoded by the IBRV gIII gene and cannot revert to the production of the IBRV gIII antigens. As a result, animals vaccinated with such can be distinguished from animals infected with field strains of IBRV so as to enable the eradication of IBR disease through the application of quarantine measures. Additionally, in the present invention, it has been possible for the first time to provide an IBR vaccine which is both distinguishable from field strains, as discussed above, and which is not only effective in controlling the spread of IBR disease, but wherein the animals vaccinated with such, due to mutations also in the IBRV tk gene, are less likely to become carriers of the vaccine virus and are unlikely to acquire a dormant infection with pathogenic field strains.

SUMMARY OF THE INVENTION

An object of the present invention is to provide an IBR vaccine effective in controlling the spread of IBR.

Another object of the present invention is to provide an IBR vaccine wherein the animal vaccinated with such is less likely to become a carrier of either the IBRV vaccine virus or an IBRV field strain.

Still another object of the present invention is to provide an IBR vaccine, wherein the IBRV vaccine virus is distinguishable from any IBRV field strain and from other IBR vaccine viruses.

A further object of the present invention is to provide an IBR vaccine, wherein animals vaccinated with such can be distinguished from animals infected with any IBRV field strain or vaccinated with other IBR vaccine viruses.

A still further object of the present invention is to provide an IBRV which fails to produce any antigenic gIII polypeptides as a result of a deletion and/or insertion mutation in the IBRV gIII gene.

An even further object of the present invention is to provide an IBR virus which both fails to produce any functional TK as a result of a mutation in the coding sequence of the IBRV tk gene and fails to produce any antigenic IBRV gIII polypeptides as a result of a deletion and/or insertion mutation in the IBRV gIII gene.

Another object of the present invention is to provide an IBR vaccine wherein animals vaccinated with such do not develop antibodies to the IBRV gIII glycoprotein.

Still another object of the present invention is to provide an IBR virus which cannot revert to tk+, is easily distinguished from tk+ virus, and cannot revert to gIII+.

Yet still another object of the present invention is to provide an IBRV which can replicate efficiently at temperatures ranging from 34.5° C. to 40° C., i.e., inclusive of temperature-resistant viruses.

An additional object of the present invention is to provide methods for the production of an IBRV which contains deletion and/or insertion mutations in the IBRV gIII gene.

Other objects of the present invention will be apparent from the detailed description of the invention hereinafter.

In an embodiment of the present invention, the above-described objects have been met by an IBRV which fails to produce any antigenic IBRV gIII polypeptides as a result of a deletion and/or insertion mutation in the IBRV gIII gene, and a vaccine for IBR disease comprising (1) a pharmaceutically effective amount of said virus and (2) a pharmaceutically acceptable carrier or diluent.

In a further embodiment of the present invention, the IBRV also fails to produce any functional TK as a result of a mutation in the IBRV tk gene.

In still another embodiment of the present invention, the IBRV mutant is a temperature-resistant virus.

In an additional embodiment of the present invention, the above-described objects have been met by a process for producing an IBRV which fails to produce any antigenic IBRV gIII polypeptides as a result of a deletion in the IBRV gIII gene comprising:

(1) Constructing a hybrid plasmid comprising a cloning vector and a DNA fragment of IBRV containing substantially all of the IBRV gIII gene and flanking sequences thereof;

(2) Deleting DNA sequences from the hybrid plasmid of step (1) such that less than substantially all of the IBRV gIII gene is present, while retaining IBRV DNA sequences adjacent to each side of the deletion;

(3) Cotransfecting, in IBRV host cells, the resulting hybrid plasmid of step (2) with infectious gIII+ IBRV DNA; and (4) Screening the progeny viruses obtained in step (3) so as to identify and produce IBRV which fail to produce any antigenic IBRV gIII polypeptides as a result of a deletion in the IBRV gIII gene.

In a further embodiment, a foreign DNA sequence is inserted in place of the deleted IBRV gIII gene sequences in step (2) such that no antigenic IBRV gIII polypeptides are produced and such that IBRV DNA sequences adjacent to each side of the deleted IBRV gIII gene sequences are retained. As a result, the IBRV mutants of step (4) fail to produce any antigenic IBRV gIII polypeptides due to combined deletion and insertion mutations in the IBRV gIII gene.

In a still further embodiment, step (2) is replaced by step (2'): Inserting a foreign DNA sequence into the plasmid of step (1) such that no antigenic IBRV gIII polypeptides are produced and such that IBRV DNA sequences adjacent to each side of the insertion are retained. As a result, the IBRV mutants of step (4) fail to produce any antigenic IBRV gIII polypeptides due to an insertion mutation in the IBRV gIII gene.

In a preferred embodiment of the present invention, the infectious gIII+ IBRV DNA of step (3) is derived from an IBRV mutant which fails to produce any functional thymidine kinase such that the resulting IBRV mutants of step (4) are both tk− and gIII−.

In a still further embodiment of the present invention, the infectious gIII+ IBRV DNA of step (3) is derived from a temperature-resistant IBRV such that the resulting IBRV mutants of step (4) are both temperature-resistant and gIII−.

BRIEF DESCRIPTION OF THE DRAWINGS

FIG. 1 shows the construction of IBRV(NG)dltkdlgIII which is obtained by cotransfection of infectious gIII+ DNA from IBRV(NG)dltk with the 6.3 kb HindIII-KpnI fragment from plasmid pLAHKdlApaI. The HindIII restriction map of IBRV(NG)dltk virus DNA is also shown in FIG. 1. As shown in FIG. 1, the IBRV tk gene deletion mutation and the (NG) sequence insertion mutation in IBRV(NG)dltk are located in the HindIII-A fragment. On the other hand, the IBRV gIII gene is located in the HindIII-I fragment. The restriction map of a portion of the HindIII-I fragment (HindIII to BglII) is enlarged at the top of FIG. 1 and shows the locations of the translational start (ATG) and polyadenylation (AATAAA) signals of the IBRV gIII gene. The HindIII restriction map of the recombinant IBRV(NG)dltkdlgIII of the present invention is also shown. The HindIII-BglII sequence that remains following the 1.53 kb ApaI deletion for plasmid pLAHK-dlApaI is shown at the bottom of FIG. 1 to illustrate the predicted restriction map in the region of the deleted IBRV gIII gene for IBRV(NG)dltkdlgIII.

FIG. 2 shows the construction of pLAHK-dlApaI which was used for the cotransfection depicted in FIG. 1 to obtain the recombinant virus IBRV(NG)dltkdlgIII. In FIG. 2, the IBRV HindIII-I fragment (11.7 kb) of IBRV(Los Angeles) (ATCC No. VR-188) (see FIG. 1 of U.S. Pat. No. 4,703,011) was first cloned in pBR322 to produce plasmid pLAH-I Then, the 7.6 kb HindIII-KpnI fragment of pLAH-I was subcloned at the HindIII-KpnI sites of plasmid pUC18dlEcoRI to obtain plasmid pLAHK. Plasmid pUC18dlEcoRI was derived from plasmid pUC18 by restriction endonuclease treatment with EcoRI, mung bean nuclease treatment, and religation. This procedure eliminated the four base overlap sequence $$\begin{pmatrix} 5'\text{-G} \downarrow \text{AATT C-}3' \\ |\ ////\ | \\ 3'\text{-CT TAA} \uparrow \text{G-}5' \end{pmatrix}$$

Figure 1:
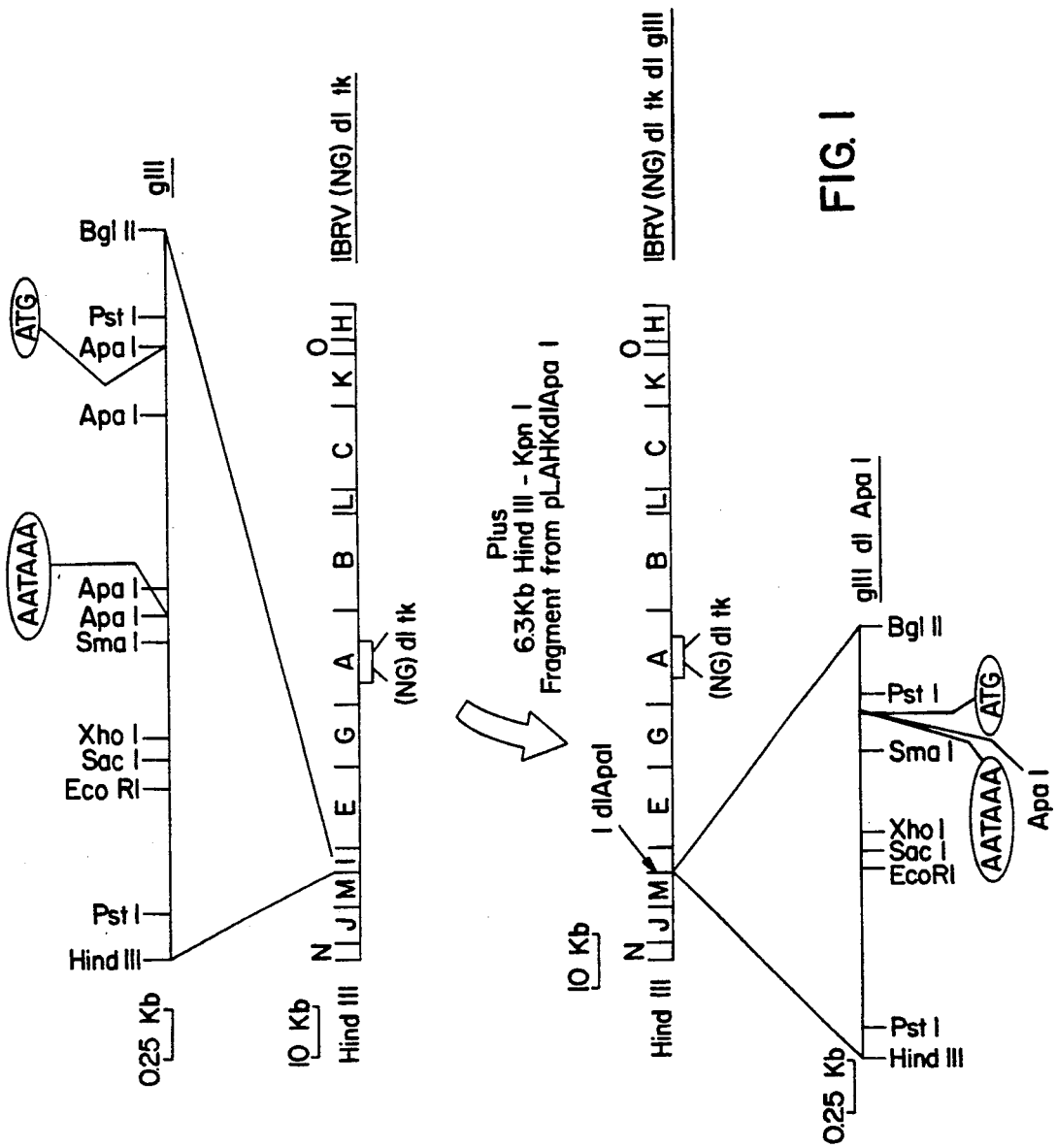
FIG. 1 schematically illustrates, by example, the derivation of IBRV of the present invention. Specifically.

of the EcoRI restriction endonuclease site but did not otherwise change plasmid pUC18. Plasmid pLAHK has only one EcoRI restriction site located in the IBRV sequence downstream from the IBRV gIII gene. The 2.5 kb EcoRI-BamHI fragment of pLAH-I was also subcloned at the EcoRI and BamHI restriction endonuclease sites of pBR322 to produce plasmid pLAEB. ApaI cleavage of pLAEB and religation resulted in the deletion of three ApaI fragments of 731, 590, and 212 bp, respectively, to produce the plasmid, pLAEBd-lApaI, with a total of 1,533 bp deleted. The ApaI deletion removes most of the coding sequences of the IBRV gIII gene (see FIG. 3). Finally, the EcoRI-BamHI fragment of pLAEBdlApaI was exchanged for the EcoRI-BamHI fragment of pLAHK to produce a deletion plasmid lacking IBRV gIII gene sequences, but retaining 5' and 3' IBRV flanking sequences to facilitate recombination with infectious gIII IBRV DNAs.

FIG. 3 illustrates the nucleotide sequence (1,975 bases) of IBRV(Los Angeles) DNA which contains the coding region of the IBRV gIII gene and flanking sequences thereof. This sequence is the complement of the DNA strand transcribed to produce the IBRV gIII mRNA. The ApaI restriction endonuclease fragments deleted from the IBRV gIII gene to obtain IBRV(NG)dltkdlgIII are shown in FIG. 3. Also in FIG. 3, the predicted amino acid sequence of the IBRV gIII polypeptide is presented in the three-letter amino acid code designation.

FIG. 4A shows ethidium bromide-stained agarose gel fragments of HindIII-digested and of BamHI plus EcoRI-digested DNA from the parental IBRV(NG)dltk virus and the recombinant IBRV isolates, E12A, C6G, and C3F. These recombinant viruses have deletions in the IBRV tk and gIII genes. Lane M shows HindIII cleaved lambda phage and HaeIII cleaved φX174 phage DNA marker fragments.

FIG. 4B shows autoradiographs demonstrating molecular hybridization of the $^{32}$P-labeled M13-38 probe to the DNA fragments of the IBRV strains shown in FIG. 4A. The M13-38 probe is a single-stranded M13mp18 DNA containing the 1.68 kb SacI fragment which spans part of the coding region and downstream sequence of the IBRV gIII gene (see FIG. 2, plasmid pLAHK).

FIG. 5A shows ethidium bromide-stained agarose gel fragments of HindIII plus BamHI-digested, PstI-digested. EcoRI-digested, and HindIII-digested DNA from the parental IBRV(NG)dltk (lanes 1, 3, 5, and 7) and the recombinant IBRV isolate, IBRV(NG)dltkd-lgIII (strain C6G) (lanes 2, 4, 6, and 8). Lane M shows HindIII cleaved lambda phage and HaeIII cleaved φX174 phage DNA marker fragments.

FIG. 5B shows autoradiographs demonstrating molecular hybridization of the 32P-labeled M18-38 probe to the DNA fragments of the IBRV strains shown in FIG. 5A.

FIG. 6A shows ethidium bromide-stained agarose gel fragments of HindIII plus BamHI-digested, PstI-digested. EcoRI-digested, and HindIII-digested DNA from the parental IBRV(NG)dltk (lanes 1, 3, 5, and 7) and the recombinant IBRV isolate, IBRV(NG)dltkd-lgIII (strain C6G) (lanes 2, 4, 6, and 8). Lane M shows HindIII cleaved lambda phage and HaeIII cleaved φX174 phage DNA marker fragments.

FIG. 6B shows autoradiographs demonstrating molecular hybridization of the $^{32}$P-labeled M13-1 probe to the DNA fragments of IBRV(NG)dltk, shown in FIG. 6A, but not to the DNA fragments of IBRV(NG)dltkd-lgIII shown in FIG. 6A. The M13-1 probe is a single-stranded M13mp19 DNA containing the 0.36 kb SalI fragment of the IBRV gIII gene (see FIG. 3, nucleotides 1,286–1,646) which is the sense-strand of the IBRV gIII gene.

Figure 7:
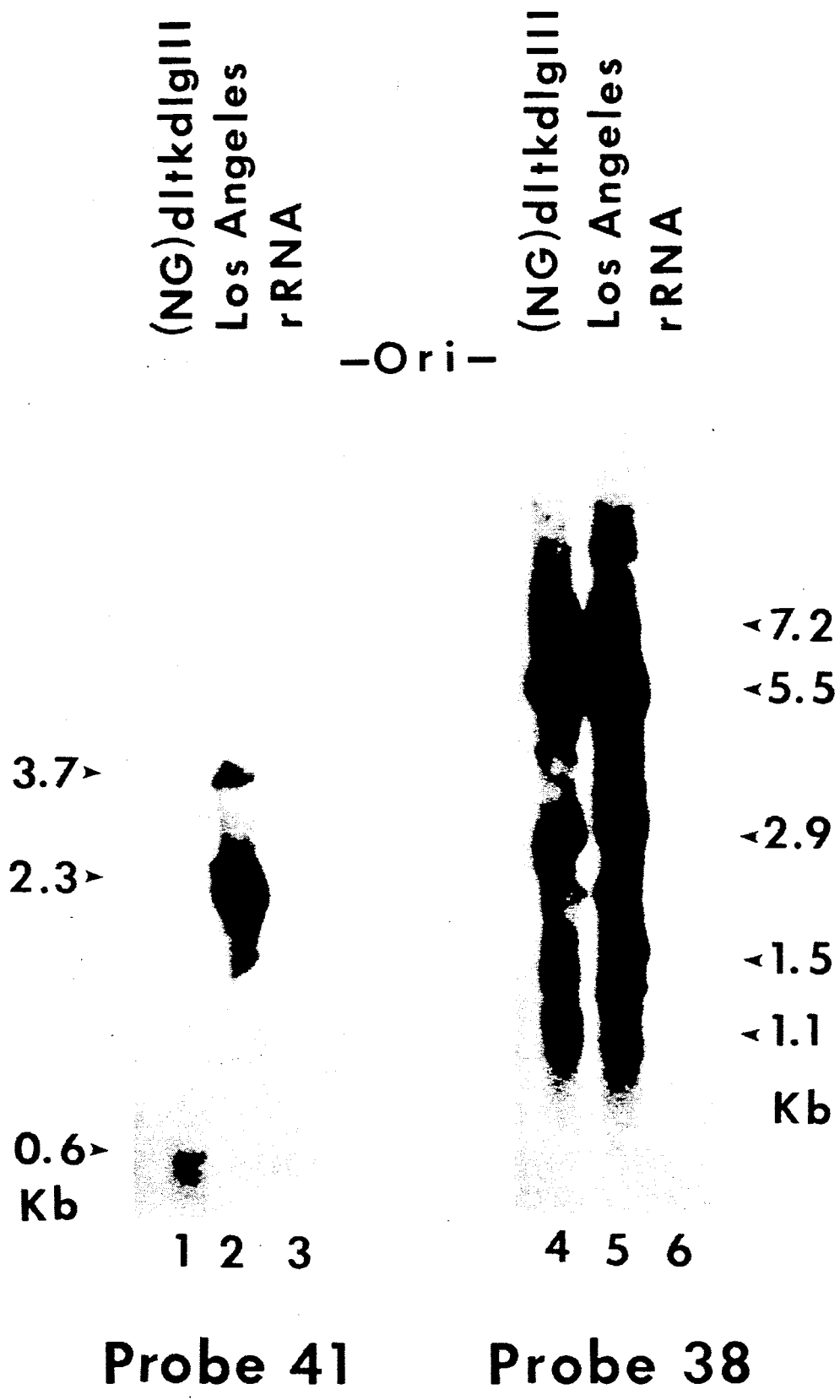

FIG. 7 illustrates molecular hybridization (Northern blotting) experiments using $^{32}$P-labeled M13-41 and M13-38 DNA probes versus mRNAs extracted from cells infected with the IBRV gIII IBRV(Los Angeles) strain and the IBRV gIII⁻recombinant, IBRV(NG)dltkdlgIII. The M13-41 probe is a single-stranded M13mp18 DNA containing the 1.86 kb SacI fragment of the IBRV gIII gene (see FIG. 2, plasmid pLAHK) which is the sense-strand of the IBRV gIII gene. The M13-38 probe is also a single-stranded M13mp18 DNA containing the 1.86 kb SacI fragment of the IBRV gIII gene, but this probe is the non-sense strand of the IBRV gIII gene. Ribosomal RNA was electrophoresed along with the mRNAs to provide molecular weight markers.

FIG. 8 illustrates immunoprecipitation experiments using polyclonal anti-IBRV bovine sera (PC-14) or monoclonal anti-gIII antibodies (MC2905) versus detergent extracts from cells infected with the gIII+ IBRV-(Los Angeles) strain or the gIII+ IBRV(Cooper) strain, or with the gIII⁻ recombinant IBRV(NG)dltkdlgIII. The mobilities of molecular weight markers are shown at the left of the figure.

DETAILED DESCRIPTION OF THE INVENTION

As discussed above, the above-described objects of the present invention have been met by an IBRV which fails to produce any antigenic IBRV gIII polypeptides as a result of a deletion and/or insertion mutation in the IBRV gIII gene, and a vaccine for IBR disease comprising (1) a pharmaceutically effective amount of said virus and (2) a pharmaceutically acceptable carrier or diluent.

In a further embodiment of the present invention, the IBRV also fails to produce any functional TK as a result of a mutation in the tk gene.

In still another embodiment of the present invention, the IBRV is a temperature-resistant virus.

In an additional embodiment of the present invention, the above-described objects have been met by a process for producing an IBRV which fails to produce any antigenic gIII polypeptides as a result of a deletion in the IBRV gIII gene comprising:

(1) Constructing a hybrid plasmid comprising a cloning vector and a DNA fragment of IBRV containing substantially all of the IBRV gIII gene and flanking sequences thereof;

(2) Deleting DNA sequences from the hybrid plasmid of step (1) such that less than substantially all of the IBRV gIII gene is present, while retaining IBRV DNA sequences adjacent to each side of the deletion;

(3) Cotransfecting, in IBRV host cells, the resulting hybrid plasmid of step (2) with infectious gIII+ IBRV DNA; and (4) Screening the progeny viruses obtained in step (3) so as to identify and produce IBRV mutants which fail to produce any antigenic IBRV gIII polypeptides as a result of a deletion in the IBRV gIII gene.

In a further embodiment, a foreign DNA sequence is inserted in place of the deleted IBRV gIII gene sequences in step (2) such that no antigenic IBRV gIII polypeptides are produced and such that IBRV DNA sequences adjacent to each side of the deleted IBRV gIII gene sequences are retained. As a result, the IBRV mutants of step (4) fail to produce any antigenic IBRV gIII polypeptides due to combined deletion and insertion mutations in the IBRV gIII gene.

In a still further embodiment, step (2) is replaced by step (2'): Inserting a foreign DNA sequence into the plasmid of step (1) such that no antigenic IBRV gIII polypeptides are produced and such that IBRV DNA sequences adjacent to each side of the insertion are retained. As a result, the IBRV mutants of step (4) fail to produce any antigenic IBRV gIII polypeptides due to an insertion mutation in the IBRV gIII gene.

In a preferred embodiment of the present invention, the infectious gIII IBRV DNA of step (3) is derived from an IBRV mutant which fails to produce any functional thymidine kinase such that the resulting IBRV mutants of step (4) are both tk− and gIII−.

In a still further embodiment of the present invention, the infectious gIII+ IBRV DNA of step (3) is derived from a temperature-resistant IBRV such that the resulting IBRV mutants of step (4) are both temperature-resistant and gIII−.

The IBRV gIII gene is approximately 1,900 bp in size (see FIG. 3) The IBRV gIII mutations of the present invention can be produced by, for example, (1) eliminating a 75 to 1,500 bp IBRV DNA fragment from an appropriate region of the IBRV gIII gene; (2) producing smaller deletions of 5, 7, 8, 10, and 11 bp or about 50 to 200 bp of IBRV DNA near the 5' end of the coding sequences, such that the translational reading frame is altered and IBRV gIII polypeptide synthesis is aborted: (3) deleting about 50 to 200 bp of IBRV DNA to eliminate the nucleotide sequences encoding the principal epitopes of IBRV gIII; (4) deleting about 10 to 200 bp of IBRV DNA and at the same time inserting a foreign DNA sequence, such that hybrid RNAs are produced which are not processed, transported, or translated properly on the polyribosomes; or (5) inserting a foreign DNA sequence, such that hybrid RNAs are produced which are not processed, transported, or translated properly on the polyribosomes.

The deletions may be produced in different ways, for example, by (1) cleaving the IBRV gIII gene inserted in a cloning vector with one or more restriction endonucleases so as to cut the IBRV gIII gene at two or more sites, and then religating so as to eliminate IBRV gIII nucleotide sequences; or (2) cleaving the IBRV gIII gene inserted in a cloning vector at one site, followed by exonuclease treatment of the IBRV gIII gene so as to extend the gap and to remove nucleotides 5' and/or 3' to the cut, and then religating.

In the present invention, the deletion mutant, IBRV(NG)dltkdlgIII, described in detail below, was produced by eliminating a 1.53 kb ApaI fragment which contains substantially all of the coding sequences of the IBRV gIII gene with the exception of the ATG translational start codon (see FIG. 3). The size of this deletion insured that (1) no polypeptide would be made with antigenic determinants, i.e., epitopes, capable of eliciting IBRV gIII antibodies in vaccinated animals, or capable of reacting with antisera to IBRV gIII glycoprotein produced in animals infected with field strains of IBRV; and (2) reversion, i.e., back mutation to an IBRV gIII−producing virus was virtually impossible. In the present invention, IBRV gIII deletion mutants are preferred due to their low reversion frequency.

As discussed above, in another embodiment, the deletion and/or insertion mutants can contain a foreign DNA sequence in place of the deleted IBRV gIII gene sequences or in addition to IBRV gIII gene sequences.

As used herein, a "foreign DNA sequence means (1) any DNA sequence which does not encode a gene, i.e., a noncoding DNA sequence, regardless of origin, such as a viral, eucaryotic, or procaryotic noncoding sequence and inclusive of oligonucleotide linkers (2) any DNA sequence which encodes a gene other than an IBRV gIII gene; i.e., a coding DNA sequence; or (3) any coding IBRV DNA sequence which has been translocated from its normal location on the IBRV genome to another location on the IBRV genome, such as the IBRV tk gene or IBRV gI gene translocated into the IBRV gIII gene.

The oligonucleotide linker is generally 8 to 10 nucleotides in length, but can be longer, e.g., about 50 nucleotides, or shorter, e.g., 4, 5, of 7 nucleotides. The preferred length of the oligonucleotide linker is about 8 to 10 nucleotides in length. The DNA sequence of the oligonucleotide linker is not critical. Similarly, the size and sequences of other foreign DNA sequences employed in the present invention is not critical. Generally, the size of foreign DNA sequences, other than oligonucleotide linkers, is about 0.5 to 5.0 kb in length. For example, the HSV-1, HSV-2, and marmoset herpesvirus tk genes are about 1.3 kb in length; the chicken and human tk genes are about 2.9 and 4.2 kb in length, respectively; the neo$^R$ gene is about 1.0 kb in length; and the lacZ gene is about 3.0 kb in length.

The method of inserting the foreign DNA sequence into the plasmid DNA will depend upon the type of foreign DNA sequence used. Palindromic double-stranded linkers containing one or more restriction nuclease sites in the oligonucleotide sequence (New England Biolabs) may be inserted by well known procedures (Maniatis, T. et al. *Molecular Cloning*, Cold Spring Harbor Laboratory (1982)). Foreign DNA sequences may also be inserted in plasmid DNA by tailing ends with complementary homopolymers using terminal transferase (Maniatis, E. et al, *Molecular Cloning*, Cold Spring Harbor Laboratory (1982)). By the judicious choice of foreign DNA sequence length, frame shift mutations may be produced in the IBRV gIII gene, augmenting the effect of deletions within the IBRV gIII gene.

The particular cloning vector employed in the present invention to construct the hybrid plasmid comprising a DNA fragment of IBRV containing substantially all of the IBRV gIII gene and flanking sequences thereof of step (1) is not critical as long as the cloning vector contains a gene coding for a selective trait, e.g., drug resistance. Examples of such cloning vectors include pBR322 and pBR322-based vectors (Sekiguchi, T. et al. *Gene*, 21:267-272 (1983)). pMB9, pBR325, pKH47, pUC18, and pUC19 (Bethesda Research Laboratories), pBR328 and pHC79 (Boehringer Manneheim Biochemicals), phage Charon 28 (Bethesda Research Laboratories), pKBll and pKSV-10 (P-L Biochemicals), pMAR420 (Otsuka, H. et al, *Virol.*, 113:196-213 (1981)) and oligo(dG)-tailed pBR322 (New England Nuclear), pBR322 is one of the preferred cloning vectors in the present invention because the 11.1 kb HindIII-I fragment contains the IBRV gIII gene and can be cloned in the single HindIII site of pBR322 (see FIG. 2). Similarly, the 2.5 kb EcoRI/BamHI fragment, which is shown in plasmid pLAH-I, contains the IBRV gIII gene and can be cloned at the unique BamHI and EcoRI sites of pBR322. Plasmid pUC18 is another preferred cloning vector in the present invention because the cloning sites of pUC18 can readily be modified, for example, to delete an EcoRI site in producing pUC18-dlEcoRI, so that the resulting plasmid contains KpnI and HindIII cloning sites for the insertion of the 7.6 kb KpnI to HindIII fragment of pLAH-I.

The specific host employed for growing the hybrid plasmids of the present invention is not critical to the present invention. Examples of such hosts include *E. coli* K12 RR1 (Bolivar, F. et al, *Gene*, 2:95-113 (1977); *E. Coli* K12 HB101 (ATCC No. 33694) *E. coli* MM21 (ATCC No. 336780); and *E. coli* DH1 (ATCC No. 33849). *E. coli* K12 RR1 is the preferred host and has an F− hsd R hsd M genotype.

Similarly, alternative vector/cloning systems can be employed such as plasmid vectors which grow in *E. coli* or *Saccharomyces cerevisiae*, or both, or plasmid vectors which grow in *B. subtilus*, or even vectors such as bovine papilloma virus (ATCC No. 371112) which grow in animal cells such as mouse (ATCC No. CRL-1616) (Elder, J. T. et al. *Ann. Rev. Gen.*, 15:295-340 (1981); and Ure, R. et al. *Methods in Enzymology*, "Recombinant DNA," Vol, 101, Part C (Academic Press. N.Y.) (1983)).

As used herein, "flanking sequences" means the sequences upstream, downstream, or both upstream and downstream, from the IBRV gIII gene coding sequences. The upstream sequences contain the transcriptional control signals, i.e., promoters and enhancers, wherein the downstream sequences contain the transcription termination and polyadenylation signals of the IBRV gIII gene.

The precise IBRV gIII gene sequences which must be present in the hybrid plasmids of steps (1) and (2) will depend on the sequences chosen for the deletion and/or insertion and the restriction endonucleases and exonucleases to be employed in the engineering of the deletion and/or insertion mutant.

The specific IBRV DNA sequences adjacent to the deletion and/or insertion in the plasmid required in step (1) will depend on the specifics of the deletion and/or insertion in the hybrid plasmid. In general, the size of the IBRV DNA sequences adjacent to both the 3' and 5' sides of the deletion and/or insertion will be at least about 400 bp. In plasmid pLAHKdlApaI (see FIG. 2), described in detail below, the 3' and 5' sequences on both sides of the deletion are about 1.6 kb and 4.5 kb in length.

The specific IBRV strain employed as a starting material in the present invention from which the IBRV DNA fragment containing the IBRV gIII gene of step (1) is obtained and from which the infectious gIII+ IBRV DNA of step (3) is obtained, is not critical. Examples of such strains include tk+ IBRV strains and tk− IBRV strains. These strains can be either non-temperature resistant or temperature resistant.

Examples of such tk+ IBRV strains include the following strains: Los Angeles strain (ATCC No. VR-188). Cooper strain (ATCC No. VR-864). IPV strain K22 (Kendrick, J. W. et al. *Cornell Vet.*, 48:458-495 (1958)), strains M03, M06, BFN-IH, BFN-IIN, BFN-IID, Gi 1 to 5, Bi, B4, BRV, LAE, V3 415, V3 416, V3 18, V3 93 (Gregersen, J-P. et al, *Arch. Virol.*, 84:91-103 (1985)). BFA Wabu strain (Ackermann, M. et al, *Vet. Microbiol.*, 9:53-63 (1984)), strain P8-2 (Weinmaster, G. A. et al. *Virol.*, 118:191-201 (1982)), strains P10, P10, and P34 (Engels, M. et al. *Arch. Virol.*, 67:169-174 (1981)), Alberta (Canada) isolates No. 1 to No. 122 (Misra, V. et al. *Arch. Virol.*, 76:341-354 (1983), or IBRV(RTK-1B) (U S. Pat. No. 4,703,011), all of which produce IBRV gIII.

Examples of such tk− IBRV strains include the temperature -resistant IBRV(B8-D53) (ATCC No. VR-2066) and IBRV(NG)dltk (ATCC No. VR-2112) strains, all of which produce IBRV gIII.

The specific IBRV host cells employed in the present invention are not critical so long as they allow for permissive growth of IBRV. Further, the IBRV host cells can be tk− IBRV host cells or tk+ IBRV host cells.

Examples of such tk+ IBRV host cells include Rab-9 (ATCC No. CRL-1414); primary rabbit kidney cells, secondary rabbit kidney cells; rabbit cornea (SIRC) cells (ATCC No. CCL-60), rabbit kidney (LLC-RKl) cells (ATCC No. CCL-106), embryo bovine trachea (EBTR) cells (ATCC No. CCL-44), bovine turbinate (BT) cells (ATCC No. CRL-1390), and bovine kidney (MDBK) cells (ATCC No. CCL-22). (The American Type Culture Collection Catalog indicates that some types of lamb, goat, cat, and horse cells may also be permissive for IBRV(Los Angeles) (ATCC No VR-188)). Rab-9 are the preferred tk+ IBRV host cells employed in the present invention. However, it should be noted that for the production of virus used for vaccination of animals in the field, a United States Department of Agriculture certified cell line permissive for IBRV, preferably of the same species as the animal to be vaccinated, and free of other infectious agents, should be used. For example, a suitable bovine cell line would be a certified diploid nontumorigenic bovine turbinate or kidney cell line free of mycoplasma and other viruses.

An example of a tk⁻ IBRV host cell which can be employed and allow permissive growth of IBRV is the rabbit Rab(BU) cell line, which was derived from Rab-9 cells (Kit, S. et al. *Virol.*, 130:381-389 (1983)). Other tk⁻ IBRV host cells of rabbit or bovine origin which can be employed in the present invention can be obtained by following, for example, the procedures previously used to isolate tk⁻ mouse, human, and rabbit cell lines (Kit, S. et al, *Exptl, Cell Res.*, 31:297-312 (1963); Kit, S. et al. *Int. J. Cancer*, 1:19-30 (1966); and Kit, S. et al. *Virol.*, 130:381-389 (1983)). Rab(BU) cells are the preferred tk⁻ IBRV host cells employed in the present invention not only because they permit the replication to high titers of both tk and tk⁻ IBRV strains, but also because they do not detectably revert to tk⁺ in selective medium comprising $10^{-4}$ M hypoxanthine; $10^{-6}$ M aminopterin; $4.0 \times 10^{-5}$ M thymidine; and $10^{-5}$ M glycine (hereinafter "HATG medium")) and they can be used for the plaque titration of IBRV at both permissive (about 34.5° C.) and nonpermissive (about 39.1° C.) temperatures. It is important that the tk⁻ IBRV host cells do not detectable revert to tk⁺ in HATG medium, because reversion to tk⁺ would interfere with autoradiographic and thymidine plaque autoradiographic assays employed to distinguish the phenotypes of tk⁺ and tk⁻ IBRVs and mixtures thereof.

The method for screening for IBRV gIII mutants in step (4) is not critical to the present invention. Screening can be performed, for example, by dot blot-molecular hybridization techniques utilizing radioactive DNA single-stranded DNA probes. These probes comprise, for example, IBRV gIII gene sequences which would be predicted to be absent from the IBRV gIII deletion mutants. IBRV gene sequences which would be predicted to be present in the IBRV gIII deletion mutants, and foreign DNA sequences which would be predicted to be present in the IBRV gIII gene insertion and deletion/insertion mutants However, those skilled in the art would recognize that molecular hybridization screening can be performed with radioactive double-stranded DNA probes, or with labeled RNA probes, such as those obtained through the use of phage T7 RNA polymerase or SP6 polymerase (Bethesda Research Laboratories and Promega Biotec), or even with nonradioactive probes, such as biotinylated nucleotide probe systems (Enzo Biochem. Inc.).

Furthermore, screening for IBRV gIII mutants in step (4) can be performed by methods other than those requiring the use of DNA or RNA probes. For example, by using monoclonal antibodies specific for the IBRV gIII glycoprotein, plaques can be screened for viruses failing to express IBRV gIII by plaque immunological procedures. In addition, by the use of anti-IBRV polyclonal sera or monoclonal antibodies specific for another IBRV glycoprotein, e.g., gI, and/or anti-foreign protein polyclonal sera or monoclonal antibodies specific for the foreign protein, plaques can be screened for viruses expressing the other IBRV proteins or foreign proteins. In this manner. IBRV gIII deletion and/or insertion mutants can be identified and isolated.

In the context of this invention, a temperature-resistant virus is a virus which is nontemperature-sensitive. Thus, a temperature-resistant virus is capable of replicating, at a nonpermissive temperature, i.e., about 38.5° C. to 40° C., preferably 39.1° C., about as well as the parental virus or field isolates of IBRV replicate at a permissive temperature. By contrast, temperature-sensitive IBRV strains contain mutations in viral genes essential for replication, whereby functional gene products are produced at permissive temperatures, i.e., about 32° C. to 37.5° C., preferably 34.5° C., but not at nonpermissive temperatures. Therefore, in temperature-sensitive viruses, production of infectious virus particles is 4 to 7 logs lower at the nonpermissive temperatures compared to production at permissive temperatures. With temperature-resistant virus strains, production of infectious virus particles is about the same at nonpermissive temperatures as at permissive temperatures.

Temperature-resistant viruses are superior to temperature-sensitive viruses as modified live virus vaccines because (1) attenuation results from alterations in pathogenic viral genes rather than from crippling viral genes required for replication; and (2) temperature-resistant viruses can be safely administered intramuscularly, intranasally, or intravenously and can replicate in the deep tissues of the body so as to elicit a more complete and prolonged immunological response.

In contrast, temperature-sensitive viruses only replicate at low temperature sites, such as the upper respiratory tract and, thus, can only be administered intranasally.

The gIII⁻ IBRV mutants of the present invention can be employed as modified-live virus vaccines against IBR disease when containing additional mutations which attenuate IBRV. Such additional mutations include tk⁻ mutations and mutations in nonessential glycoprotein genes other than gIII. For example, an IBRV gene which is located in the $U_S$ region of the IBRV genome and which is homologous to the PRV gI gene and the HSV gE gene may be nonessential for virus replication and may be mutated without impairing the protective properties of the vaccine (Longnecker, R. et al. *Science*, 236:573-576 (1987); and Petrovskis, E. A. et al. *Virol.*, 159:193-195 (1987)).

Alternatively, the gIII⁻ IBRV mutants of the present invention can be employed as killed virus vaccines against IBR disease. That is, inactivation of infectivity by ultraviolet light or formaldehyde treatment of the gIII⁻ IBRV mutants yields a vaccine capable, after intraperitoneal administration, of eliciting cytotoxic T cells and protective antibodies against virion proteins. Animals immunized with this vaccine would thus be protected against virulent virus infections.

Furthermore, nonionic detergent extracts (Nonidet P40 or Triton X-100) can be made from gIII⁻IBRV-infected bovine cells to produce subunit IBRV vaccines. These extracts contain all of the glycoproteins and nonglycoproteins encoded by the IBRV strain employed with the exception of glycoprotein gIII. After purification of the glycoproteins, they can be employed as subunit vaccines (Hilleman, M. R. et al. In: *The Human Herpesvirus: An Interdisciplinary Perspective*, Eds, Nahmias, A. J. et al (Elsevier, N.Y.), page 503 (1981); Eisenberg, R. J. et al. *J. Virol.*, 41:1099-1104 (1982); Long, D. et al. *Inf. Immun.*, 37:761-764 (1984); and Dix, R. D. et al. *J. Med, Virol.*, 17:9-18 (1985)).

As another alternative, the gIII⁻ IBRV mutants of the present invention can be employed as a starting material to obtain the tk⁻ IBRV mutants described in U.S. Pat. No. 4,703,011.

A pharmaceutically effective amount of the above-described viruses of the present invention can be employed along with a pharmaceutically acceptable carrier or diluent as a vaccine against IBR disease in animals such as bovine, sheep, goats and swine.

Examples of pharmaceutically acceptable carriers or diluents useful in the present invention include any physiological buffered medium, i.e., about pH 7.0 to 7.4, containing from about 2.5 to 15% (v/v) serum which does not contain antibodies to IBRV, i.e., is seronegative for IBRV Agammaglobulin serum is preferred to serum which contains gammaglobulin. Examples of serum to be employed in the present invention include swine serum, calf serum, fetal calf serum, horse serum, and lamb serum. Agammaglobulin swine serum from pigs seronegative for IBRV is preferred for vaccination of swine. Agammaglobulin fetal calf serum or agammaglobulin calf serum from calves seronegative for IBRV is preferred for vaccination of calves. Serum protein such as porcine albumin or bovine serum albumin in an amount of from about 0.5 to 3.0% (w/v) can be employed as a substitute for serum. However, it is desirable to avoid the use of foreign proteins in the carrier or diluent which will induce allergic responses in the animal being vaccinated.

The virus may be diluted in any of the conventional stabilizing solutions containing phosphate buffer, glutamate, casitone, and sucrose or sorbose, or containing phosphate buffer, lactose, dextran and glutamate.

It is preferred that the viruses of the present invention be stored at a titer of at least $10^5$ to $10^6$ p.f.u./ml at $-70°$ C. to $-90°$ C. or in a lypholized state at $4°$ C. to $-20°$ C. The lypholized virus may be reconstituted for use with sterile distilled water or using an aqueous diluent containing preservatives such as gentamycin and amphotericin B or penicillin and streptomycin.

The useful dosage to be administered will vary depending upon the age, weight, and species of the animal vaccinated and the mode of administration. As a modified-live virus vaccine, a suitable dosage can be, for example, about $10^{4.5}$ to $10^7$ p.f.u./animal, preferably about $10^{4.5}$ to $10^{5.5}$ p.f.u./animal. As a killed vaccine, a suitable dosage can be, for example, about ten-fold greater than that employed for a modified-live virus vaccine.

The vaccines of the present invention can be administered intramuscularly and subcutaneously. Intramuscularly is the preferred mode of administration. The modified-live vaccines of the present invention can also be administered intranasally.

The following examples are provided for illustrative purposes only and are in no way intended to limit the scope of the present invention.

In the following examples, all media and buffer solutions were made up in glass distilled water unless otherwise indicated.

EXAMPLE 1

Production of gIII⁻ IBRV Mutants

A. Growth Medium for Tissue Culture Cells

Rab-9 cells (ATCC No. CCL-1414) (tk+ host cells were propagated in a temperature-controlled. $CO_2$ incubator, in Eagle's minimum essential medium (hereinafter "APMEM") (Flow Laboratories, Inc.) supplemented with 10% (v/v) bovine fetal serum (hereinafter "BFS") or 10% (v/v) lamb serum, 20 mM bicarbonate, plus 10 mM Hepes (pH 7.3), and 2.0 mM tamine plus 50 µg/ml neomycin. This medium will be referred to hereinafter as "growth medium".

Rab(BU) cells (Kit, S. et al. Virol., 130:301-389 (1983)) (tk⁻ host cells) were grown in the same growth medium as the Rab-9 cells, but which was supplemented with 25 µg/ml of BrdUrd. However, the growth medium was not supplemented with BrdUrd for the passage immediately preceeding the plaque autoradiography experiment described in Section Q. below and for carrying out the plaque autoradiography experiments described in Section Q. below.

B. Purification of IBRV DNA

IBRV DNA was prepared essentially as described by Pignatti et al for the preparation of HSV DNA (Pignatti, P. F. et al. Virol., 93:260–264 (1979)).

More specifically, 20 eight-ounce prescription glass bottle monolayer cultures of Rab-9 cells (about $5 \times 10^6$ cells/culture) containing 20 ml of growth medium were infected at a multiplicity of infection (hereinafter "m.o.i.") of 5.0 p.f.u./cell of IBRV and incubated for 3 hr at $34.5°$ C., at which time cellular DNA synthesis had been inhibited by the viral infection. Then 1.0 µCi/ml and 0.25 µg/ml of 3H-thymidine was added to radioactively label the viral DNA and incubation was continued at $34.5°$ C. for 17 hr more. The cells were dislodged from the glass by scraping into the growth medium with a rubber policeman, centrifuged at $600 \times g$, washed with ice cold phosphate buffered saline solution comprising 14 M NaCl, 0.003 M KCl, 0.001 M $CaCl_2$ 0.0005 M $MgCl_2$, and 0.01 M phosphate (pH 7.5) (hereinafter "PBS"), containing 10 µg/ml nonradioactive thymidine, Next, the cells were centrifuged at $600 \times g$ and then frozen in an ethanol-dry ice bath.

After thawing, the cell pellet (about 0.7 ml) was resuspended in 9 volumes of lysing solution comprising 0.25%(w/v) Triton X-100, 10 mM EDTA, 10 mM Tris-HCl (pH 7.9). Next, the cell suspension was transferred to a Dounce homogenizer, and incubated at room temperature for 20–30 min with gentle mixing.

Then, the cell suspension was transferred to a glass centrifuge tube and NaCl was added to a final concentration of 0.2 M. Next, the tube was inverted several times, and the solution was immediately centrifuged at $1,000 \times g$ at $4°$ C. for 10 min.

The resulting supernatant was decanted into a glass tube and deproteinized by incubating with 100 µg/ml proteinase K (E. M. Science) in buffer comprising 10 mM Tris-HCl (pH 7.5), 1.0 mM EDTA (hereinafter "TE buffer") for 1 hr at $37°$ C. Then, 1 volume of 90% (v/v) redistilled phenol was added, the solution was mixed by inversion, centrifuged at $20,000 \times g$, and the aqueous phase, i.e., top phase, was transferred to a polyallomer centrifuge tube. Solid sodium acetate was then added to a concentration of 4.0% (w/v), the nucleic acids were precipitated with 2 volumes of ice cold ethanol, and incubated overnight at $-20°$ C. Thereafter, the precipitate was collected by centrifugation at 16,000 rpm at $4°$ C. in a Spinco SW25 rotor, dissolved in 2.0 ml TE buffer, and dialyzed at $4°$ C. against TE buffer.

The resulting DNA solution was then transferred to a polyallomer centrifuge tube and CsCl in TE buffer to 57% (w/w) ($\rho = 1.715$ g/cm²). Next, the DNA was centrifuged for 46 hr at $22.5°$ C. at 44,000 rpm in a Spinco No. 50 Ti rotor. Then, 12 drop fractions were collected from the bottom of the polyallomer tube and aliquots of 4.0 µl were counted in a liquid scintillation spectrometer to locate the IBRV DNA containing fractions ($\rho$ = about 1.727 g/cm² ). When a total of 25 fractions were collected, generally fractions 13-15 contained the IBRV DNA.

The IBRV DNA-containing fractions were then pooled and dialyzed against several changes of TE buffer at 4° C. for about 24 hr. The concentration of DNA was determined fluorometrically. The IBRV DNA yield was about 25 μg from $10^8$ cells.

The identity of IBRV DNA was verified by the pattern of restriction endonuclease-digested IBRV DNA fragments obtained after electrophoresis at 4° C. in a submarine gel apparatus (Bethesda Research Laboratories, Inc.).

More specifically, the resulting DNA was cleaved with BamHI, SalI, KpnI, or HindIII restriction endonucleases under the reaction conditions recommended by the manufacturer (New England Biolabs, Inc.). Next, 1/10 volume of a solution comprising 0.4% (w/v) bromphenol blue, 125 mM EDTA, and 50% (v/v) glycerol was added to terminate the reaction, followed by heating at 65° C. for 10 min. 20 μl aliquots of each sample was applied into the sample wells of an agarose gel and electrophoresis was carried out as described below.

Electrophoresis of restriction endonuclease fragments was carried out on 0.6% (w/v) agarose slab gels (Kit, S. et al. *J. Med. Virol.*, 12:25-36 (1983)) in buffer comprising 30 mM $NaH_2PO_4$, 1.0 mM EDTA, 40 mM Trizma-base (pH 8.1) (hereinafter "electrophoresis buffer") at 45 volts, 4° C. for 16 hr. After electrophoresis, DNA fragments were stained by soaking the gel in electrophoresis buffer containing 0.5 μg/ml ethidium bromide, visualized over a long wave UV illuminator, and photographed. The restriction endonuclease map for the HindIII fragments of the IBRV(NG)dltk strain is shown in FIG. 1.

IBRV DNA prepared in this manner had an infectivity of about 100 to 1,000 p.f.u./μg DNA in the standard transfection assay.

C. Cloning of the IBRV DNA

The HindIII fragments of DNA from IBRV(Los Angeles) (ATCC No. VR-188) were cloned at the HindIII cleavage site of pBR322 by the following procedure.

4.0 μg of IBRV(Los Angeles) DNA was dissolved in buffer comprising 50 mM NaCl, 50 mM Tris-HCl (pH 8.0), 10 mM $MgCl_2$, and 100 μg/ml of bovine serum albumin (hereinafter "BSA") (hereinafter "HindIII cutting buffer"). The DNA was then digested at 37° C. for 1 hr with 40 units of HindIII (New England Biolabs, Inc.). The reaction was terminated by adding an equal volume of 90% (v/v) redistilled phenol, mixing, and centrifuging for phase separation. After dialysis of the aqueous phase against 1×TE buffer, sodium acetate was added to 0.1M followed by the addition of 2 volumes of ethanol, and the DNA precipitate was stored at −20° C. overnight. The DNA precipitate was collected by centrifugation and dissolved in 1.0×TE buffer.

The restriction endonuclease fragments thus obtained were then combined in the following manner with pBR322 which had been cleaved with HindIII and dephosphorylated:

4.0 μg of HindIII-digested IBRV(Los Angeles) DNA was mixed with 0.5 μg of HindIII digested and dephosphorylated pBR322 DNA (New England Biolabs, Inc.), in 0.05 ml of a solution comprising 50 mM Tris-HCl (pH 7.8), 10 mM $MgCl_2$, 20 mM dithiothreitol, 1.0 mM 50 μg/ml of BSA (hereinafter "ligation buffer"), and 1,000 units of phage T4 DNA ligase (New England Biolabs, Inc.), and incubated overnight at 4° C. The reaction was terminated by adding EDTA to 20 mM and heating at 65° C. for 10 min. The hybrid plasmid DNA was diluted in TE buffer and used to transform *E. coli* K12 RR1 bacteria as described below (Bolivar, F. et al. *Gene*, 2:95-113 (1977)).

Bacteria were prepared for transformation using $CaCl_2$ (Mandel, M. et al. *J. Mol. Biol.*, 53:159-162 (1970)). Specifically, an overnight culture at a density of 2.0 ($A_{600}$) of *E. coli* K12 RR1 was used to inoculate 200 ml of broth comprising 1.0% (w/v) bactotryptone, 0.5% (w/v) yeast extract, and 0.5% (w/v) NaCl (hereinafter "ML broth"), at a bacterial density of 0.02 ($A_{600}$) The bacteria were incubated for about 2 hr until a density of about 0.5 ($A_{600}$) was achieved. The bacteria were then pelleted by centrifugation and resuspended in ¼ volume of ice cold 50 mM $CaCl_2$ After a 5 min incubation on ice, the bacteria were again pelleted and resuspended in 1/40 the volume of ice cold 50 mM $CaCl_2$.

Next, 0.1 ml of the hybrid plasmid DNA, about 10-100 ng, in TE buffer was added to 0.2 ml of the $CaCl_2$-treated bacteria. The mixture was kept at 4° C. for 30 min. Then, the temperature was raised to 37° C. for 5 min and 0.3 ml of ML broth was added. Thereafter, incubation was continued for 45 min at 37° C. with gentle shaking. Samples were plated on trypticase soy agar plates (BBL Microbiology Systems) supplemented with 30 μg/ml ampicillin.

Rapid screening of the resulting clones for the desired hybrid plasmid DNA (hereinafter "rapid screening procedure") was conducted as follows:

An overnight culture of bacteria containing hybrid plasmid DNA was inoculated into 5.0 ml of ML broth containing 30 μg/ml ampicillin and incubated at 37° C. to a density of about 1.5 ($A_{600}$) 1.0 ml of this bacterial culture was then transferred to a 1.5 ml Eppendorf polypropylene tube and centrifuged in an Eppendorf centrifuge for about 1 min at room temperature to pellet the bacteria. Next, the bacteria were resuspended in 0.1 ml of buffer comprising 2.0 mg/ml egg lysozyme, 50 mM glucose, 10 mM cyclohexanediamine tetraacetate (hereinafter "CDTA"), and 25 mM Tris-HCl (pH 8.0) (hereinafter "lysozyme solution No. 1") and then incubated for 30 min at 4° C. Next, 0.2 ml of 0.2 N NaOH plus 1.0% (w/v) sodium dodecylsulfate (hereinafter "SDS") was added to the bacterial suspension and the tube was vortexed and kept at 4° C. for 5 min. Thereafter, 0.15 ml of 3.0M sodium acetate (pH 4.8) was added, and the tube was gently inverted, during which time a "clot" of DNA formed. The DNA was kept at 4° C. for 1 hr to allow chromosomal DNA, protein, and high molecular weight RNA to precipitate. Next, the precipitate was centrifuged in an Eppendorf centrifuge for 5 min at room temperature and the clear supernatant fluid, approximately 0.4 ml, containing hybrid plasmid DNA was transferred to a second Eppendorf centrifuge tube. Then, 2½ volumes of ethanol (approximately 1.0 ml) were added to the second tube which was placed at −20° C. for 30 min. The precipitated hybrid plasmid DNA was collected by centrifugation for 2 min at room temperature in an Eppendorf centrifuge. Then, the hybrid plasmid DNA was dissolved in 0.1 ml of a solution comprising 0.1M sodium acetate and 0.05M Tris-HCl (pH 8.0), reprecipitated with ethanol, collected by again centrifuging, and finally dissolved in 100 μl of 0.1×TE buffer.

Then, a 10 μl aliquot of hybrid plasmid DNA was diluted in 50 μl HindIII cutting buffer and 2.0 units of HindIII were added. Following a digestion period of 60 min at 37° C., the sample was mixed with 1/10 volume of a solution comprising 0.4% (w/v) bromphenol blue, 125 mM EDTA, and 50% (v/v) glycerol, and about 20 μl of the resulting solution was applied to an 0.6% (w/v) agarose slab gel for electrophoretic analysis as described above. This analysis revealed whether the hybrid plasmid contained a HindIII insert and, if so, the size, in kb, of the insert (Birnboim, H. C. et al. *Nucl. Acids Res.*, 7:1513-1523 (1973)).

Figure 2:
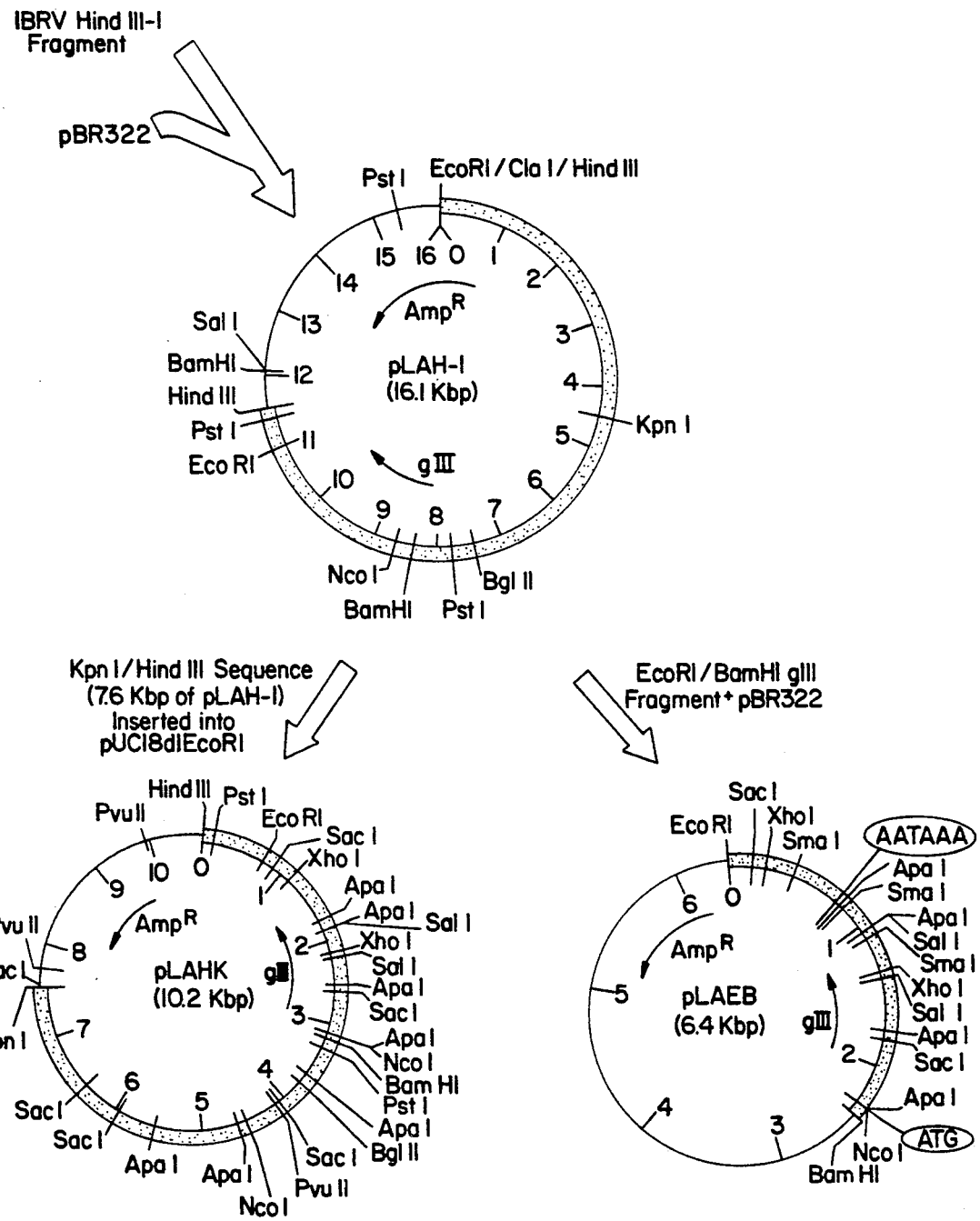
FIG. 2 schematically illustrates, by example, the derivation of plasmids employed in the present invention. Specifically.
Figure 2:
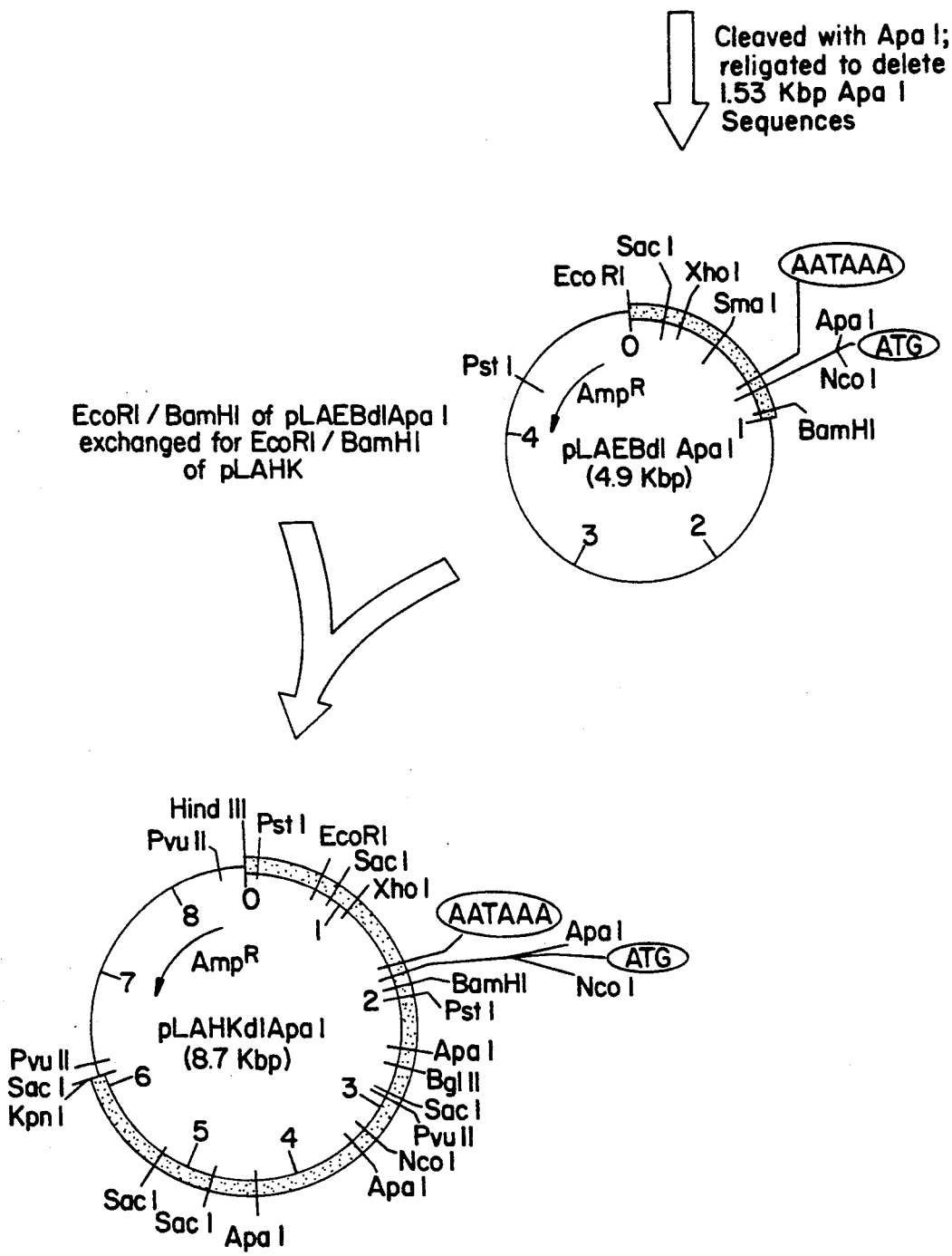

In this manner, a 16.1 kb plasmid containing an 11.7 kb HindIII insert, which comigrated with the IBRV HindIII-I fragment in agarose gel electrophoresis, was isolated and designated pLAH-I (see FIGS. 1 and 2).

For large-scale preparation of hybrid plasmid DNA, 200 times the amount of hybrid plasmid-transformed bacteria were processed as compared with the bacteria used to produce hybrid plasmid DNA for the rapid screening procedure described above, except that after the first ethanol precipitation, the sample was treated at 37° C. for 30 min, with 0.5 mg of pancreatic RNase A (Worthington Biochemical Corp,) from a stock solution comprising 1.0 mg/ml RNase A in 5.0 mM Tris-HCl (pH 8.0), which had been heated at 100° C. for 10 min. The treatment was followed by the addition of 500 μg of proteinase K (E. M. Science) in TE buffer at 37° C. for 30 min. Subsequently, an equal volume of phenol was added, and the sample was vortexed and centrifuged as described above to separate the phases. The aqueous phase was then removed, precipitated with ethanol, and collected by centrifugation as described above. Next, the precipitate was dissolved in 0.2 ml of TE buffer and layered on a 10.4 ml linear 10–40% (w/v) sucrose gradient in 50 mM NaCl, 10 mM Tris-HCl (pH 7.5), 1.0 mM EDTA, and centrifuged at 4° C. for 20 hr at 24,000 rpm in a Spinco SW41 rotor, 15 drop fractions were collected from the bottom of polyallomer centrifuge tubes into wells of plastic trays. A total of 35 fractions was obtained, 5.0 μl aliquots were then screened by employing agarose gel electrophoresis as described above. Fractions containing hybrid plasmid DNA were pooled, dialyzed against 0.1×TE buffer, and stored at 4° C. for further studies.

D. Mapping of the Structural Gene for IBRV gIII

Previous studies had shown that the PRV g92 gene is homologous to the HSV-1 and HSV-2 gC genes (Robbins, A. K. et al. *J. Virol.*, 58:339-347 (1986); and Kit, S. et al. *Am. J. Vet. Res.*, 48:780-793 (1987)) and also that the varicella-zoster gpV (No. 14) gene is homologous to the HSV-1 gC gene (Davison, A. J. et al. *J. Gen. Virol.*, 67:1759-1816 (1986)). The PRV g92 gene is not essential for growth of PRV in cultured cells and mutants of PRV which does not express PRV g92 have been constructed (Kit, S. et al. *Am. J. Vet. Res.*, 48:780-793 (1987); and U.S. patent application Ser. No. 823,439, filed Jan. 28, 1986). Therefore, the PRV g92 gene may also be homologous to an IBRV glycoprotein gene which is not essential for growth in cultured cells and this IBRV glycoprotein gene might be detected by means of molecular hybridization (Southern blotting) with radioactive PRV g92 DNA probes.

To test this hypothesis, a 0.4 kb KpnI/BamHI fragment of the PRV g92 gene was subcloned in phage M13mp19 and a single-stranded $^{32}$P-labeled probe was prepared (U.S. patent application Ser. No. 823,439, filed Jan. 28, 1986). Southern blotting analyses with the PRV g92 gene (0.4 kb KpnI/BamHI) probe demonstrated molecular hybridization under stringent hybridization conditions to the cloned HindIII-I fragment of IBRV DNA in pLAH-I (see FIGS. 1 and 2), Stringent hybridization was carried out as described in detail in Section L. below. Additional molecular hybridization experiments revealed that the sequences homologous to the PRV KpnI/BamHI probe were located within a 2.5 kb BamHI/EcoRI fragment of pLAH-I. As described in Section E, below, this 2.5 kb BamHI/EcoRI fragment was subcloned at the BamHI and EcoRI site of pBR322 and the resulting plasmid was designated pLAEB (see FIG. 2). The PRV KpnI/BamHI probe also strongly hybridizes to pLAEB under stringent hybridization conditions. Furthermore, the location of the 2.5 kb IBRV BamHI/EcoRI fragment of pLAEB mapped at a location on the IBRV genome (0.11 to 0.12 map units) homologous to the location of the gC gene on the HSV-1 genome and the g92 gene in the PRV genome. Therefore, the IBRV gIII gene was found to be homologous to the PRV g92 gene and the HSV-1 gC gene.

E. Construction of pLAEB

The following steps in Sections E. to G. were carried out in order to subclone the IBRV gIII gene from pLAH-I to pBR322 and to delete substantially all of the IBRV gIII coding sequences from the subcloned IBRV gIII DNA.

1.0 μg of pBR322 and 1.0 μg of pLAH-I were mixed and digested with 40 units of BamHI in 20 μl of buffer comprising 150 mM NaCl, 6.0 mM Tris-HCl (pH 8.0), 6.0 mM MgCl$_2$, 100 μg/ml of BSA at 37° C. for 1 hr, and then with 40 units of EcoRI in 100 μl of buffer comprising 50 mM NaCl, 100 mM Tris-HCl (pH 7.5), 5.0 mM MgCl$_2$, 100 μg/ml of BSA at 37° C. for 1 hr. The cleaved DNAs were extracted with an equal volume of phenol:chloroform (1:1) and precipitated with 2 volumes of ethanol, ligated with phage T$_4$ ligase to transform CaCl$_2$-treated *E. coli* K12 RR1 cells as described above. Ampicillin-resistant colonies were screened for the presence of a 6.4 kb plasmid. This plasmid was designated pLAEB. Restriction endonuclease analyses of the plasmid confirmed the structure of pLAEB shown in FIG. 2.

F. Nucleotide Sequence of the IBRV gIII gene

The nucleotide sequence of the 2.5 kb BamHI/EcoRI fragment plus the nucleotide sequence of the 0.6 kb fragment extending 5 from the BamHI site to the BglII site of pLAEB was determined as described below (see FIGS. 1 and 2).

Portions of the IBRV nucleotide sequence of pLAH-I extending from the BamHI to BglII restriction sites (see FIGS. 1 and 2) were subcloned in the double-stranded, replicative form (RF) of phage M13mp18 and M13mp19 (Hu, N. T. et al. *Gene*, 17:271-272 (1982); and Messing, J. et al. *Gene*, 19:269-276 (1982)). The use of these two phages permitted the cloning of small overlapping DNA fragments in two orientations. Then, replication of the recombinant phage M13 derivatives in *E. coli* K12 JM103 bacteria (New England Biolabs, Inc.) resulted in the synthesis of single-stranded phage DNA which could be used for sequencing reactions. Sequencing reactions were carried out by the conventional dideoxynucleotide chain termination method (Sanger, F. et al. *J. Mol. Biol.*, 143:161-178 (1980): and Sanger, F. et al. *Proc. Natl. Acad. Sci, USA*, 74:5436-5467 (1977)). The reaction mixture contained a single-stranded phage M13mp18 or M13mp19 subclone of IBRV DNA as template, either an M13 pentadecamer primer (New England Biolabs, Inc.) or synthetic oligonucleotide primer sequences of IBRV DNA made with the automated DNA synthesizer-Microsyn 1450 (Systec, Inc.) to initiate DNA synthesis on each of the templates, ($\alpha$-$^{32}$P)dTTP as the labeled substrate, $Mg^{++}$, the appropriate unlabeled deoxyribonucleoside triphosphates and dideoxyribonucleoside triphosphates, and *E. coli* DNA polymerase. Klenow fragment (Bethesda Research Laboratories). After incubating the reaction mixture for 15 min at 38° C., a chase solution containing nonradioactive deoxyribonucleoside triphosphates was added. The reaction was terminated after 10 min at 38° C. by adding 10 μl of a 12.5 mM EDTA solution containing 0.3M sodium acetate and 200 μg of yeast tRNA (Sigma Chemical Co.). The reaction products were precipitated with ethanol, dissolved in 10 μl of a solution comprising 90% (v/v) formamide, 30 mM NaOH, 10 mM EDTA, 0.3% (w/v) bromphenol blue, and 0.3% (w/v) xylene cyanol, heated for 1 min at 90° C., and loaded into 8.0% (w/v) sequencing gels comprising 7.6% (w/v) acrylamide, 0.4% (w/v) bisacrylamide, 0.003% (w/v) TEMED, and 0.007% (w/v) ammonium persulfate.

The nucleotide sequence of the IBRV gIII gene obtained thereby is shown in FIG. 3. Restriction nuclease cleavage sites predicted from the nucleotide sequence are presented in Table 1 below.

TABLE 1

RESTRICTION NUCLEASE CLEAVAGE SITES PREDICTED FROM THE NUCLEOTIDE SEQUENCE OF THE IBRV gIII GENE

| Restriction endonuclease | Location of first nucleotide in sequence (Nucleotide No.) |
|---|---|
| ApaI | 319, 909, 1640, 1854 |
| BalI | 70 |
| BamHI | 254 |
| MstI | 891 |
| NaeI | 1169, 1429 |
| NcoI | 315 |
| PstI | 164 |
| PvuI | 948 |
| SacI | 833 |
| SacII | 58, 698, 905 |
| SalI | 1286, 1646 |
| ScaI | 1200 |
| XhoI | 1328 |
| XhoIIA | 254 |

The nucleotide sequence contains one open reading from (509 codons) which can encode a 54,621 dalton molecular weight polypeptide. By comparison, the homologous PRV g92 polypeptide consists of 479 codons and has a predicted molecular weight of 50,860 daltons (Robbins, A. K. et al, *J. Virol.,* 58:339-347 (1986)).

The translational initiation codon (ATG) is found 63 nucleotides downstream from the BamHI site. The open reading frame of 1,527 nucleotides is followed by a termination codon (TAG) ten nucleotides upstream from an ApaI site (see FIG. 3). A polyadenylation signal (AATAAA) is present 68 nucleotides downstream from the TAG termination codon. TATA and CAAT transcriptional signal sequences are present 5' to the ATG initiation codon. The nucleotides CCGCC and GGC, respectively, which precede and follow the ATG translational start codon, are the same as the consensus sequences implicated as playing a role in the efficiency of translation (Kozak, M., *Microbiol. Rev.,* 47:1-45 (1984); and Kozak, M., *Nature,* 308:241-246 (1984)). The nucleotide sequence, 5'-GACGGGCCCGTCGACTACACCTGC-3' at 1,320 nucleotides downstream from the ATG translational start codon and 208 nucleotides upstream from the TAG termination codon is identical to that of the PRV g92 gene at 1,270 nucleotides downstream from the ATG translation start codon and also 208 nucleotides upstream from the PRV g92 termination codon.

The predicted amino acid sequence for the IBRV gIII polypeptide encoded by the IBRV gIII gene shown in FIG. 3 has features in common with envelope glycoproteins of other herpesviruses. The first 21 amino acids are hydrophobic with the exception of arginine at position 6. This sequence could correspond to a signal peptide for membrane insertion and may well be removed during translation and transport. Amino acids present at positions 481-498 are also strongly hydrophobic and have the characteristics of a membrane-spanning region. The carboxy terminal 11 amino acids have a basic charge and may function as a cytoplasmic anchor sequence. Finally, four potential glycosylation sites (Asn-X-Ser/Thr) are present in the region between the putative signal sequence and the transmembrane sequence.

G. Construction of pLAEBdlApaI 1.0 μg of pLAEB was digested with 20 units of ApaI in 20 μl buffer comprising 6.0 mM NaCl, 6.0 mM Tris-HCl (pH 7.4), and 6.0 mM $MgCl_2$, 6.0 mM 2-mercaptoethanol, 100 μg/ml of BSA at 37° C. for 1 hr. The cleaved DNA was extracted with an equal volume of phenol:chloroform (1:1) and precipitated with 2 volumes of etnanol, ligated with phage $T_4$ ligase, and used to transform $CaCl_2$-treated *E. coli* K12 RR1 cells as described above. Ampicillin-resistant colonies were screened for a plasmid which was smaller than pLAEB by about 1.5 kb. This plasmid was designated pLAEBdlApaI. Restriction endonuclease analyses of the plasmid confirmed the structure of pLAEBdlApaI shown in FIG. 2.

H. Construction of pUCl8dlEcoRI

Plasmids pUC18 and pUC19 are well known cloning vectors commercially available from Bethesda Research Laboratories. They contain the PvuII/EcoRI fragment of pBR322. This fragment carries the ampicillin-resistance gene ($\beta$-lactamase) and the origin of DNA replication A HaeII fragment (coordinates 240-685) containing a portion of the lacZ gene $\beta$-galactosidase) and a multiple cloning site of M13mp18 or M13mp19 sequencing vectors has been combined with the pBR322 fragment to form the original pUC vector from which pUC18 and pUC19 were derived. DNA fragments may be inserted into the unique restriction endonuclease sites located in the multiple cloning region. Insertion is monitored by the loss of $\beta$-galactosidase activity upon transformation of the appropriate host strains. Plasmids pUC18 and pUC19 contain the same restriction endonuclease sites in the multiple cloning region but in opposite orientations.

For the purposes of the present constructions, the pUC18 cloning vector was first modified, as described below, to remove the EcoRI cloning site because the EcoRI site in the HaeII fragment would have interfered with subsequent steps in the subcloning of the IBRV gIII gene.

More specifically, 1.0 μg of pUC18 was incubated with 20 units of EcoRI in 20 μl of buffer comprising 50 mM NaCl, 100 mM Tris-HCl (pH 7.5), 5.0 mM $MgCl_2$, 100 μg/ml of BSA at 37° C. for 1 hr. The EcoRI-digested pUC18 was incubated with 300 units of mung bean nuclease (Pharmacia) in 100 μl of buffer comprising 50 mM NaCl, 30 mM sodium acetate (pH 4.6), 1.0 mM ZnCl$_2$, at 37° C. for 10 min, extracted once with phenol:chloroform (1:1), and precipitated with 2 volumes of ethanol. Then, ligation was carried out 40 μl of a buffer comprising 800 units of phage T$_4$ ligase (New England Biolabs), 50 mM Tris-HCl (pH 7.8), 10 mM MgCl$_2$, 20 mM dithiothreitol, 1.0 mM ATP, and 50 μg/ml of BSA, at 4° C. for 18 hr. Ligated DNA was used to transform CaCl$_2$-treated *E. coli* K12 RR1 cells as discussed above. Ampicillin-resistant colonies were propagated and the plasmids were analyzed by digesting with EcoRI, HindIII, KpnI, and PstI. The plasmid thus obtained had lost the EcoRI site but retained all of the other restriction endonuclease sites of pUC18. This plasmid was designated pUC18dlEcoRI.

I. Construction of pLAHK

The purpose of this step was to transfer the KpnI/HindIII fragment of pLAH-I, which contains the IBRV gIII gene, to pUC18dlEcoRI (see FIG. 2).

1.0 μg of pUC18dlEcoRI and 1.0 μg of pLAH-I were mixed and digested with 40 units of KpnI in 20 μl of buffer comprising 6.0 mM NaCl, 6.0 mM Tris-HCl (pH 7.5), 6.0 mM MgCl$_2$, 1.0 mM dithiothreitol, of BSA at 37° C. for 1 hr, and then with 40 units of HindIII in 100 μl of buffer comprising 50 mM NaCl, 50 mM Tris-HCl (pH 8.0), 10 mM MgCl$_2$, 100 μg/ml of BSA at 37° C. for 1 hr. The cleaved DNAs were extracted with an equal volume of phenol:chloroform (1:1) and precipitated with 2 volumes of ethanol, ligated with phage T$_4$ ligase, and used to transform CaCl$_2$-treated *E. coli* K12 RR1 cells as described above. Ampicillin-resistant colonies of transformed *E. coli* K12 RR1 were screened for the presence of a 10.2 plasmid. This plasmid was designated pLAHK. Restriction endonuclease analyses of the plasmid confirmed the structure of pLAHK shown in FIG. 2.

J. Construction of pLAHKdlApaI

The purpose of the step was to exchange the EcoRI/BamHI site of pLAEBdlApaI for the EcoRI/BamHI site of pLAHK (FIG. 2). Unlike pLAEBdlApaI, pLAHKdlApaI contains a long 3.0 kb IBRV nucleotide flanking sequence 5' to the ATG translational start signal of the IBRV gIII gene. Therefore, pLAHKdlApaI is more useful than pLAEBdlApaI for the transfer of the IBRV gIII deletion mutation into a gIII IBRV homologous recombination.

1.0 μg of pLAHK and 1.0 μg of pLAEBdlApaI were mixed and digested with BamHI and then with EcoRI as described above. The cleaved DNAs were ligated and used to transform CaCl$_2$-treated *E. coli* K12 RR1 cells as described above. Ampicillin-resistant colonies were screened for a plasmid which was smaller than pLAHK by 1.5 kb. This plasmid was designated pLAHdlApaI. Restriction endonuclease analyses of the plasmid confirmed the structure of pLAHKdlApaI shown in FIG. 2.

K. Construction of IBRV(NG)dltkdlgIII

To obtain IBRV(NG)dltkdlgIII, which is tk$^-$ IBRV and fails to produce any antigenic IBRV gIII polypeptides as a result of a deletion in the IBRV gIII gene, the infectious gIII+ DNA of the tk$^-$ IBRV(NG)dltk strain (ATCC No. VR-2112) was coinfected with the 6.3 kb HindIII-KpnI fragment derived from plasmid pLAHK-dlApaI (see FIGS. 1 and 2) as described in U.S. Pat. No. 4,514,497 and U.S. Pat. No. 4,703,011.

More specifically, 10 μg of pLAHKdlApaI was digested with 50 units of KpnI in 20 μl of buffer comprising 6.0 mM NaCl, 6.0 mM Tris-HCl (pH 7.5), 6.0 mM MgCl, 1.0 mM dithiothreitol, and 100 μg/ml of BSA at 37° C. for 90 min. The DNA was precipitated with 2 volumes of ethanol, redissolved in 50 μl of buffer comprising 50 units of HindIII, 50 mM NaCl, 50 mM Tris-HCl (pH 8.0), 10 mM MgCl, and 100 μg/ml of BSA, and incubated at 37° C. for 90 min. The reaction mixture was extracted with phenol:chloroform (1:1) and dialyzed extensively against 0.1×TE buffer. The digested plasmid DNA was diluted in 0.1 TE buffer to 10 μg/ml and filter sterilized.

Rab-9 cells were seeded in 60 mm Petri dishes (2×10$^5$ cells per 5.0 ml of growth media per dish) and incubated at 37° C. for 48 hr. Then, the following sterile solutions were added to a test tube in sequential order.

(1) 0.02 ml of 50 μg/ml of IBRV(NG)dltk DNA in TE buffer;

(2) 0.2 ml of 10 μg/ml of plasmid pLAHKdlApaI cleaved with KpnI and HindIII in 0.1 TE buffer;

(3) 0.65 ml of water;

(4) 1.0 ml of 20 μg/ml of salmon sperm DNA in 2×Hepes buffer solution comprising 16 g/l NaCl, 0.74 b/l KCl, 0./25 g/l Na$_2$HPO$_4$.H$_2$O, 2.0 g/l glucose, 10 g/l Hepes (pH 7.05) (hereinafter "2×Hepes buffer solution"); and (5) 0.13 ml of 2.0M CaI$_2$.

The resulting solution was mixed by inversion and kept at room temperature for 30 min while a DNA-calcium phosphate precipitate formed. Then, 0.5 ml of the suspension was added directly to Rab-9 cells in the Petri dishes. The cells were incubated at 37° C. for 5 hr. Then, the growth media was aspirated, and the monolayer rinsed with 5.0 ml of fresh growth media, followed by the addition of 1.0 ml of a solution of 1×Hepes buffer solution plus 15% (v/v) glycerol. After a 3 min incubation at room temperature, the solution was aspirated, the monolayer rinsed with growth media again, and 5.0 ml of fresh growth media added. The cultures were incubated at 34.5° C. for 3 days until extensive cytopathic effects occurred. The cultures were frozen and stored at −80° C. The virus harvest was then titrated in Rab-9 cells under a 0.5% (w/v) agarose in growth media overlay.

L. Screening for IBRV gIII Mutants

The progeny virus obtained from the cotransfection in Section K, above mainly comprised parental IBRV(NG)dltk and a small population of homologous recombinants in which substantially all of the coding sequence of the IBRV gIII gene was deleted. To identify and screen for recombinant viruses among parental viruses, molecular hybridization experiments were carried out using a $^{32}$P-labeled IBRV gIII gene probe which hybridized to the wild-type tk+ IBRV(Los Angeles) virus and to the parental tk$^-$ IBRV(NG)dltk, but not to recombinant viruses with deletions in the IBRV gIII gene.

More specifically, the virus harvest from the cotransfection in Section K. above was thawed, sonicated, and diluted in growth media to about 100 p.f.u./ml. Rab-9 cells, seeded in 60 mm Petri dishes at 2×10$^5$ cells per 5.0 ml growth media per dish and incubated at 37° C. for 48 hr, were infected with 0.2 ml of diluted virus stock for 1 hr, overlayed with 0.5% (w/v) agarose in growth media, and incubated at 34.5° C. for 3 days. Plaques were visualized by adding a second 0.5% (w/v) agarose in growth media overlay containing 0.01% (w/v) Neutral Red and incubating at 34.5° C. overnight. Viruses were isolated from individual plaques by stabbing with sterilized toothpicks and then infecting Rab-9 cells, which had been seeded in the wells of 96-well tissue culture clusters (Costar) at $2 \times 10^4$ cells per 0.2 ml growth media per well and incubated at 37° C. for 48 hr, 480 clones of progeny viruses from individual plaques were isolated ($5 \times 96$-well tissue culture clusters). The 96-well tissue culture clusters were incubated at 34.5° C. for 3 days and stored at $-80°$ C., and served as master plates.

Rab-9 cells were seeded in $10 \times 96$-well tissue culture clusters as described above, incubated at 37° C. for 48 hr, and each well was infected with 50 $\mu$l of growth media from the well of the master plates (in the same location). Two copies were made from each master plate and incubated at 34.5° C. for 48 hr. The growth media was removed by aspiration and 50 $\mu$l of 0.5 N NaOH was added to each well to lyse the cells and release the DNA. After incubating at room temperature overnight, 75 $\mu$l of 1.0M Tris-HCl (pH 7.5) and 125 $\mu$l of $20 \times$SSC buffer comprising 3.0M NaCl, 0.3M sodium citrate (pH 7.0), were added to each well.

Nitrocellulose filters in a 96-well Schleicher and Schuell (Keene, N. H.) filtration apparatus was used for dot blot analysis. The filters were washed with water and with $1 \times$SSC prior to the addition of the DNA samples to the filters, the nitrocellulose filters were dried and then heated at 80° C. for 2 hr in a vacuum desiccator. The filters were placed in a plastic sealable pouch containing 50 ml of $3 \times$SSC, 0.02% (w/v) Ficoll, 0.02% (w/v) BSA, 0.02% (w/v) polyvinylpyrrollidone, 50 $\mu$g/ml of boiled and alkali-denatured salmon sperm DNA (hereinafter "modified Denhardt's solution"), and 10 $\mu$g/ml of poly(A), and incubated overnight at 60° C. with shaking. Salmon sperm DNA was added from a stock solution of about 5.0 mg/ml prepared by dissolving 50 mg of salmon sperm DNA in 10 ml of 0.2M NaOH, heating at 100° C. for 20 min to denature and shear the DNA to about 0.4 kb segments, and then neutralizing with 0.2 ml of 10M HCl.

The modified Denhardt's solution was then replaced with 50 ml of buffer comprising 50% (v/v) formamide, 0.6M NaCl, 0.2M Tris-HCl (pH 8.0), 0.02M EDTA, 0.1% (w/v) SDS, 50 $\mu$g/ml of alkali denatured salmon sperm DNA, and 10 $\mu$g/ml of poly(A) (hereinafter "hybridization buffer"). The bag was sealed using an Oster Touch-a-matic Bag Sealer and incubated at 37° C. for 1 hr on a shaker. $^{32}$P-labeled single-stranded M13 probes, obtained as described in Section M. below, were added to the bag (about $10^7$ cpm/ml/bag) and incubated at 37° C. for up to 48 hr on a shaker to allow for hybridization After hybridization had been accomplished, the bag was cut and the solution was decanted. The filters were then carefully removed and placed into a tray containing about 100 ml of hybridization buffer. The filters were washed for 30 min at 37° C. five times with gentle shaking, and then washed for 30 min at 37° C. with $0.3 \times$SSC and then placed on a filter paper to dry overnight at room temperature. For autoradiography, the filters were covered with Saran-Wrap and exposed to Fuji X-ray film with an intensifying screen for 1 to 2 days at $-80°$ C.

Two dot blots from each candidate virus were prepared. One was hybridized with probe M13-1 and the other with probe M13-38. The M13-1 probe was single-stranded M13mp19 DNA containing a 0.36 kb SalI fragment of the IBRV gIII coding region. The M13-38 probe was single-stranded M13mp18 DNA containing a 1.68 kb SacI fragment which spans a portion of the coding region and downstream sequence of the IBRV gIII gene. The M13-1 probe hybridized with wild-type gIII+ IBRV strains, but did not hybridize with the recombinants which lacked the coding region of the IBRV gIII gene. However, it was difficult to identify the recombinant viruses by the M13-1 probe alone because many wild-type viruses gave false negatives. This was probably due to the variability of the yield of viruses in each well. Poorly grown wild-type viruses gave weak hybridization signals. The M13-38 probe hybridized with both wild-type gIII+ and recombinant gIII− viruses. By comparing the dot blots hybridized with the M13-1 probe with those hybridized with the M13-38 probe, the gIII− IBRV recombinants were identified more conclusively since the recombinants gave strong signals with the M13-38 probe but no signal with the M13-1 probe, while gIII+ IBRV viruses gave strong signals with both probes or, in case of poor growth, gave poor signals with both probes.

Three clones of recombinant viruses were isolated from the 480 candidates. The clones were designated El$_2$A., CG6 and C3F.

M. Preparation of Probes for Molecular Hybridization

DNA fragments cloned in M13 phage for sequencing the IBRV gIII gene were used to make single-stranded DNA probes as described by Hu, N. T. et al. *Gene,* 17:271-277 (1982).

The SalI fragment of the IBRV gIII gene (nucleotide 1,286–1,646 in FIG. 3) was cloned in phage M13mp19. The sense-strand, which codes for mRNA of the IBRV gIII gene was cloned in M13mp19 to produce probe M13-1 and the nonsense-strand was cloned in M13mp19 to produce probe M13-4. The SalI fragment is located inside of the coding region of the IBRV gIII gene. Deletion of ApaI fragments from the IBRV gIII gene also deletes the SalI fragment. Hence, probes M13-1 and M13-4 hybridize with IBRV(NG)dltk, pLAEB, and pLAHK but do not hybridize with IBRV(NG)dltkdlgIII, pLAEBdlApaI, and pLAHKdlApaI.

The SacI fragment (nucleotide 833–2,510 in FIG. 3; see also pLAEB) was cloned in phage M13mp18. The sense-strand was cloned in M13mp18 to produce probe M13-41 and the nonsense-strand was cloned in M13mp18 to produce probe M13-38. Since the SacI fragment spans a part of the coding region and flanking sequences 3' downstream of the IBRV gIII gene, probes M13-38 and M13-41 hybridize with not only pLAEB, pLAHK, and IBRV(NG)dltk but also with their ApaI deletion derivatives, pLAEBdlApaI, pLAHKdlApaI, and IBRV(NG)dltkdlgIII. Since probe M13-41 was the sense-strand of the IBRV gIII gene, it was used to hybridize with mRNA of the IBRV gIII gene in Section O.

To prepare the probes, 2.0 $\mu$g of purified single-stranded DNA was annealed with 5.0 ng of M13 hybridization probe primer in 30 $\mu$l of buffer comprising 83 mM NaCl, 10 mM Tris-HCl (pH 7.5), 10 mM MgCl, 20 mM dithiothreitol, at 65° C. for 10 min, cooled to room temperature, and then the following substances were added, 20 $\mu$l of (about 400 mCi/mmole, 10 mCi/ml in a stabilized aqueous solution, Amersham), 20 $\mu$l of $^{32}$P)dCTP (about 400 mCi/mmole, 10 mCi/ml in a stabilized aqueous solution, Amersham), 1.0 μl of 10 mM dATP, 1.0 μl of 10 mM dGTP and 4 units of *E. coli* DNA polymerase, large fragment (Klenow enzyme, Bethesda Research Laboratories). The reaction mixture was incubated at room temperature for 2 hr, 10 μl of 0.25M EDTA was added, and the mixture was heated at 65° C. for 10 min. The labeled probe was purified by Sephadex G-50 column chromatography (0.5×15 cm). This procedure routinely yields probes with a specific activity of more than $10^8$ cpm/μg DNA.

N. Analyses of Purified DNA From the Recombinant Viruses

Viral DNA of high purity was prepared from the three clones of recombinant viruses E12A, C6G and C3F as described above. The obtained DNAs were digested with HindIII or BamHI plus EcoRI, and the restriction endonuclease fragments were separated by electrophoresis at 35 volts at 4° C. for 16 hr on a 0.6% (w/v) agarose gel submerged in a buffer comprising 0.04M Trizma base, 0.03M $NaH_2PO_4$ and 0.01M EDTA (pH 8.1). As a control. DNA from the parental virus tk− IBRV(NG)dltk, was treated in the same manner.

The resulting gel was stained with 0.5 μg/ml of ethidium bromide in electrophoresis buffer and photographed on a UV transilluminator. The results, which are shown in FIG. 4A, demonstrate that the HindIII restriction endonuclease profiles of the three recombinants, E12A, C6G and C3F, and the parental DNA were similar except that a 10.5 kb fragment was present in the recombinant virus DNAs but absent in the parental virus DNA and the amount of an 11.1 kb fragment in the parental virus DNA was greater than in the recombinant virus DNAs. This indicates that the 11.1 kb fragment in the parental tk− IBRV(NG)dltk DNA contained two different fragments which could not be separated in this gel electrophoresis system, and that one of the fragments which contains the IBRV gIII gene was reduced in size to 10.5 kb in the recombinant virus. FIG. 4A also demonstrates that the three recombinants. E12A, C6G and C3F, had an identical restriction endonuclease profile after HindIII or EcoRI plus BamHI digestion. Double digestion of parental virus DNA with BamHI plus EcoRI yielded a 2.5 kb fragment which contained the IBRV gIII gene. This fragment was not present in the recombinant virus DNAs. However, a 1.1 kb fragment, which is 1.4 kb shorter than the parental 2.5 kb fragment, was present in the recombinant virus DNAs. This fragment was barely detectable in the ethidium bromide-stained gels (see FIG. 4A), but is readily observable after Southern blotting (see FIG. 4B). These results indicate that the IBRV gIII gene in the recombinant virus was reduced in size by 1.4 kb.

One of the recombinant, C6G, and the parental tk− IBRV(NG)dltk DNA were further analyzed. DNAs from this recombinant virus and tk− IBRV(NG)dltk were digested with HindIII, EcoRI, BamHI plus HindIII, and PstI, and duplicate samples were subjected to agarose gel electrophoresis as described above. The results are shown in FIGS. 5A and 6A. As shown in FIGS. 5A and 6A, the changes in the HindIII fragments were the same as shown in FIG. 4A. In addition, as shown in FIGS. 5A and 6A, an 18.5 kb EcoRI fragment and a 3.2 kb Pstl fragment of the parental virus were reduced in size to 17.0 kb and 1.7 kb fragments, respectively, in the recombinant virus. C6G.

After electrophoresis, the gels from all three electrophoresis analyses were also placed in a glass baking tray containing 1.0M KOH for 30 min at room temperature and then in a buffer comprising 1.0M Tris-HCl (pH 7.0) and 0.6M NaCl for 60 min at room temperature. The treated gels were then transferred to a blot apparatus (Bethesda Research Laboratories). A nitrocellulose filter was prewetted in water for 10 min, in 20×SSC for 5 min, and placed on the gel. Using 20×SSC as the transfer fluid, blotting was allowed to proceed for about 24 hr. The adherent gel was removed from the nitrocellulose filter, and the filter was rinsed with 6×SSC, dried at room temperature overnight, and then baked in a vacuum desiccator at 80° C. for 2 hr. The nitrocellulose filters were placed in plastic bags, pretreated at 60° C. overnight with 50 ml of modified Denhardt's solution and with hybridization buffer at 37° C. for 1 hr as described above. The nitrocellulose filters from the three separate gels were hybridized with either M13-38 or the M13-1 probes. The procedures for the hybridization and washing were the same as described above. The results are shown in FIGS. 4B, 5B and 6B.

FIGS. 4B and 5B show the autoradiograms obtained after hybridization with the M13-38 probe. FIG. 6B shows the autoradiograms after hybridization with the M13-1 probe. As shown in FIG. 6B, the M13-1 probe did not hybridize to any of the restriction endonuclease fragments of the recombinant C6G virus DNA, while the probe did hybridize with an 11.1 kb HindIII fragment, an 18.5 kb EcoRI fragment, a 3.2 kb PstI fragment, and a 3.3 kb BamHI plus HindIII fragment of the parental tk− IBRV(NG)dltk virus DNA. As shown in FIG. 5B, the M13-38 probe not only hybridized with the same restriction endonuclease fragments, with which the M13-1 probe hybridized, but also hybridized with a 9.6 kb HindIII fragment, a 17 kb EcoRI fragment, a 1.7 kb FstI fragment, and a 1.8 kb BamHI plus HindIII fragment of the recombinant C6G virus DNA. As shown in FIG. 4B, the M13-38 probe also hybridized with the 10.4 kb HindIII fragments and the 1.1 kb BamHI plus EcoRI fragments of the C6G, E12A and C3F recombinant virus candidates, as expected.

These results conclusively demonstrate that the recombinant viruses lacked an about 1.5 kb sequence from the coding region of the IBRV gIII gene and that the recombinants were produced by homologous recombination between the parental tk− IBRV(NG)dltk and pLAHKdlApaI.

Clone C6G was selected for further study, designated IBRV(NG)dltkdlgIII, and deposited with the American Type Culture Collection (ATCC No. VR-2181).

O. Analyses of mRNA Produced in Bovine Kidney Cells Infected With IBRV(NG)dltkdlgIII Bovine kidney cells (hereinafter "MDBK cells") (ATCC No. CCL-22) were inoculated in roller bottles (10×42 cm) at $10^7$ cells per 200 ml of growth media per bottle and incubated at 37° C. for 4 days. Then, the growth media was removed, and the monolayer cultures were infected at 37° C. for 1 hr with a 10 ml suspension of IBRV(Los Angeles) or IBRV(NG)dltkdlgIII at an m.o.i. of 5.0 p.f.u./cell. Next, 100 ml of fresh growth media was added to each roller bottle and incubation was continued at 37° C. for 9 hr. At the end of the incubation period, the growth media was decanted and the infected cells were dissolved in situ in 8.0 ml of buffer comprising 6.0M guanidium isothiocyanate, 5.0 mM sodium citrate (pH 7.0), 0.1M 2-mercaptoethanol, and 0.5% (w/v) sarcosyl, and transferred to a test tube. The viscous solution was passed through a 20Gl½ needle several times to reduce the viscosity. CsCl (1.0 g of CsCl per 2.5 ml of the solution) was added, and the solution was layered above a 1.5 ml cushion of 5.7M CsCl in 0.1M EDTA (pH 7.5) in a polyallomer tube. The tubes were centrifuged in a Beckman SW 41.1 rotor at 39,000 rpm for 20 hr at 20° C. The supernatant was carefully removed by pipetting and the RNA precipitate was dissolved in 5.0 ml of buffer comprising 10 mM Tris-HCl (pH 7.4), 5.0 mM EDTA and 1.0% (w/v) SDS. The RNA solution was extracted once with 5.0 ml of a 4:1 mixture of chloroform and 1-butanol, and the aqueous phase was transferred to a fresh tube. The organic phase was re-extracted with 3.0 ml of buffer comprising 10 mM Tris-HCl (pH 7.4), 5.0 mM EDTA and 1.0% (w/v) SDS. The two aqueous extracts were combined, 0.1 volume of 3.0M sodium acetate (pH 5.2) and 2.2 volumes of ethanol were added, the materials were stored at −20° C. for 2 hr, and then the RNA precipitate was collected by centrifugation at 10.000×g for 20 min.

Polyadenylated (polyA) RNA was selected as described by Aviv, H. et al, *Proc. Natl. Acad. Sci, USA*, 69:1408–1412 (1972). More specifically, oligo(dT)-cellulose (Type 2. Collaborative Research, Inc.) was suspended in buffer comprising b 20 mM Tris-HCl (pH 7.6), 0.5M LiCl, 1.0 mM EDTA, and 0.2% (w/v) SDS (hereinafter "loading buffer") and a 1.0 cm column was prepared in a disposable polypropylene column (Bio-Rad). The column was washed successively with 3.0 ml of a solution comprising 0.1M NaOH and 5.0 mM EDTA, with water until the pH of the column effluent was less than 8.0 and with 5.0 ml of loading buffer. RNA (up to 20 μg) dissolved in 1.0 ml of water was heated at 65° C. for 5 min, 1.0 ml of 2×loading buffer was added, then cooled to room temperature, and applied to the column. The flow through fraction was collected, heated again at 65° C. for 5 min, cooled, and re-applied to the same column. The column was washed with 10 ml of loading buffer, followed by 4.0 ml of loading buffer containing a reduced concentration of LiCl, i.e., 0.1M LiCl. The poly(A) RNA was eluted with 3.0 ml of buffer comprising 10 mM Tris-HCl (pH 7.5), 1.0 mM EDTA, and 0.05% (w/v) SDS, and precipitated from the eluted fraction by adding 0.1 volume of 3.0M sodium acetate (pH 5.2) and 2.2 volumes of ethanol and keeping at −20° C. for 2 hr. The RNA precipitates were collected by centrifugation at 10,000×g for 10 min and dissolved in 100 μl of water.

The resulting poly(A) RNA (up to 20 μg) was incubated at 50° C. for 1 hr in 16 μl of buffer comprising 1.0M glyoxal, 50% (v/v) dimethylsulfoxide, and 10 mM NaH (pH 7.4), and cooled to room temperature. Then, 4.0 μl of a solution comprising 50% (v/v) glycerol, 10 mM $NaH_2PO_4$ (pH 7.0), and 0.4% (w/v) bromophenol blue was added, and the RNA was loaded onto a 1.1% (w/v) agarose gel (20×25 cm) submerged in 10 mM $NaH_2PO_4$ (pH 7.4), and electrophoresed at 35 volts for 24 hr. As molecular weight markers phage lambda DNA cleaved with HindIII was treated with glyoxal as described above and electrophoresed side by side with the RNA samples. The electrophoretic mobility of denatured DNA in this condition is about the same as that of RNA of the same size.

After electrophoresis, the gel was blotted on a nitrocellulose sheet using the DNA Blot Transfer System (Bethesda Research Laboratories). The blots were dried at room temperature and baked in a vacuum desiccator at 80° C. for 2 hr. Hybridizations were carried out with M13-38 and M13-41 probes as described above. The molecular weight markers were detected by hybridizing with nick-translated phage lambda DNA.

As discussed above, the M13-38 and M13-41 probes are single-stranded M13mp18 DNAs containing a 1.68 kb sequence which spans a portion of the coding region and downstream sequence of the IBRV gIII gene. Since the sense strand (coding strand) of the IBRV gIII gene was cloned in probe M13-41, it was predicted that probe M13-41 would hybridize with the mRNA of the IBRV gIII gene coded by wild-type IBRV(Los Angeles). Having lost the coding region of the IBRV gIII gene, but retaining the regulatory region at the 5' end of the initiation codon and the poly(A) signal (AATAAA) at the 3 end of the IBRV gIII coding regionIBRV(NG)dltkdlgIII would be expected to code for an mRNA which was shorter than the wild-type mRNA by about 1.5 kb. The results are shown in FIG. 7.

As shown in FIG. 7, the M13-41 probe hybridized with a 2.3 kb mRNA of IBRV(Los Angeles)-infected cells. This mRNA was not present in IBRV(NG)dltkd-lgIII-infected cells. Instead, the M13-41 probe hybridized to an about 0.6 kb mRNA from IBRV(NG)dltkd-lgIII-infected cells. Therefore, it is concluded that the 2.3 kb mRNA was coded by the wild-type IBRV gIII gene, and the 0.6 kb mRNA was coded by an IBRV gIII gene having the coding sequences deleted therefrom. Also as shown in FIG. 7, the M13-41 probe hybridized with a 3.7 kb mRNA of IBRV(Los Angeles)-infected cells less intensely than with the 2.3 kb mRNA. The 3.7 kb mRNA was not present in IBRV(NG)dltkd-lgIII-infected cells. It is not clear whether the 3.7 kb mRNA was also coded by the IBRV gIII gene or by some other IBRV gene partially overlapping the IBRV gIII gene.

Furthermore, as shown in FIG. 7, the M13-38 probe, which hybridized with the noncoding strand of the IBRV gIII gene, did not hybridize with IBRV gIII mRNA, i.e., the 0.6, 2.3 and 3.7 kb mRNAs, but did hybridize with 7.2, 5.5, 2.9, 1.5, and 1.05 kb mRNAs of both IBRV(Los Angeles) and IBRV(NG)dltkdlgIII. These latter mRNAs are probably coded from the complementary strand of the gene(s) located downstream from the 3' end of the IBRV gIII gene.

O. $^3$H-Mannose-Labeled IBRV gIII From Extracts of IBRV(NG)dltkdlgIII-Infected Cells MDBK cells were seeded in four-ounce bottles at $10^6$ cells per 10 ml of growth media per bottle and incubated at 37° C. for 2 days. Then, the MDBK cells were infected with IBRV(Los Angeles), the parental virus from which IBRV(NG)dltk was obtained, or with IBRV(Cooper) or IBRV(NG)dltkdlgIII at an m.o.i. of about 5.0 p.f.u./cell at 37° C. for 1 hr. The growth media was then removed, and the monolayers were washed with glucose-free growth media, 4.0 ml of glucose-free growth media supplemented with 2.0% (v/v) dialyzed fetal calf serum and 100 μCi of $^3$H-D-(2,6 3H)-mannose (54 Ci/mmole, Amersham, England) was added and the infected cell cultures were incubated at 34.5° C. for 20 hr. The growth media was removed by aspiration and 400 μl of buffer comprising 1.0% (w/v) Nonidet P40, 0.0625M Tris-HCl (pH 7.0), and 0.9% (w/v) NaCl, was added. The cell suspension was frozen at −80° C., thawed, transferred to a 1.5 ml Eppendorf centrifuge tube, and sonicated, 7.0 μl of the extract was mixed with 30 μl of anti-IBRV serum (FC-14) (serum from a cow naturally infected by IBRV in the feed lot, kindly provided by Dr. S. McConnell), or with 5.0 μl of a monoclonal antibody (IgG2a) IBRV gIII (MC2905) (provided by Dr. G. J. Letchworth) (Marshall, R. L. et al, *J. Virol.*, 57:745–753 (1986)), and the mixture was kept 4° C. for 18 hr. Next, 150 μl of Pansorbin (formalin-fixed *Staphylococcus aureus* cells, Calbiochem) was added, and the mixture was incubated at 4° C. for 45 min, and then centrifuged at 10,000 g at 4° C. for 10 min. The supernatant was removed and the pellet was resuspended in 300 μl of 0.05% (w/v) Tween 20 in PBS, and washed 3 times by repeated centrifugations. Finally, the pellet was suspended in 60 μl of buffer comprising 0.06M Tris-HCl (pH 8.9), 2.0% (w/v) SDS, 4.0% (v/v) 2-mercaptoethanol, 15% (v/v) glycerol, 0.05% (w/v) bromophenol blue, heated in a boiling water bath for 3 min, centrifuged, and the supernatant was subjected to 7.5% (w/v) SDS-polyacrylamide gel electrophoresis analysis (U.S. patent application Ser. No. 823,439, filed Jan. 28, 1986: and Kit, S. et al. *Am. J. Vet. Res.*, 48:780–793 (1987)). After electrophoresis, the gels were impregnated with an autoradiograph enhancer (Autofluor) (National Diagnostics), dried, and exposed to Fuji X-ray films at −80° C. The results are shown in FIG. 8.

As shown in FIG. 8, the anti-IBRV bovine serum (PC-14) precipitated all of the major glycoproteins of wild-type IBRV in the IBRV-infected cell extracts, except that the 92 kD to 97 kD molecular weight glycoproteins (IBRV gIII) were not precipitated from the IBRV(NG)dltkdlgIII-infected cell extract. Also, as shown in FIG. 8, the monoclonal antibody (MC2905) precipitated the 92 kD molecular weight glycoprotein, and its 79 kD precursor protein, from IBRV(Los Angeles)-infected or IBRV(Cooper)-infected cell extracts, but no polypeptide was precipitated from the extracts of mock-infected or IBRV(NG)dltkdlgIII-infected cells. These results demonstrate that IBRV(NG)dltkdlgIII fails to produce any antigenic IBRV gIII polypeptides (92 kD to 97 kD molecular weight).

Q. TK Activity of IBRV Strains

To verify that the double deletion mutant, IBRV(NG)dltkdlgIII, lacked the ability to induce functional TK activity, thymidine plaque autoradiography experiments were carried out in tk− Rab(BU) cells as described in Kit, S. et al. *Am. J. Vet. Res.*, 48:780–793 (1987): and U.S. Pat. No. 4,514,497. These experiments demonstrated that mock-infected tk− Rab(BU) cells did not have virus plaques and did not incorporate ³H-thymidine into cellular DNA. However, tk+ IBRV-(Los Angeles)-infected and tk− IBRV(NG)dltkdlgIII-infected Rab(BU) had many plaques. Plaques made by the progeny of tk+ IBRV(Los Angeles) were labeled with ³H-thymidine, but plaques made by the progeny of tk− IBRV(NG)dltkdlgIII were not labeled with ³H-thymidine. These results demonstrate that IBRV(NG)dltkdlgIII (ATCC No. VR-2181), like its parentIBRV(NG)dltk (ATCC No. VR-2112), fails to produce any functional TK activity.

R. Temperature Resistance of IBRV Strain

To verify that IBRV(NG)dltkdlgIII was temperature-resistant, the following experiments were carried out. Replicate, subconfluent monolayer cultures of MDBK cells were infected with the wild-type IBRV(Los Angeles) or with IBRV(NG)dltkdlgIII at an m.o.i. of about 0.01 p.f.u./cell and incubated in a $CO_2$ incubator at 34.5° C. and 39.1° C. Virus harvests were prepared at 3 hr and at 48 hr after infection and plaque-titrated at 34.5° C. and 39.1° C. in MDBK cells as described in U.S. Pat. No. 4,514,497. Approximately $10^3$ p.f.u./ml of virus was obtained when harvests were prepared at 3 hr after infection. This represents the virus present immediately after the absorption and penetration of the input virus. The results are shown in Table 2 below.

TABLE 2

REPLICATION FOR 48 HR AT 37.5° C. OF WILD-TYPE AND MUTANT IBRV STRAINS

| Virus | Temperature of virus growth | Virus yield (p.f.u.) when plaque titrated at: | |
|---|---|---|---|
| | | 34.5° C. | 39.1° C. |
| IBRV(Los Angeles) | 34.5° C. | $7.7 \times 10^7$ | $1.1 \times 10^8$ |
| | 39.1° C. | $3.9 \times 10^7$ | $5.6 \times 10^7$ |
| IBRV(NG)dltkdlgIII | 34.5° C | $2.1 \times 10^8$ | $2.5 \times 10^8$ |
| | 39.1° C | $5.1 \times 10^7$ | $8.4 \times 10^7$ |

Table 2 above demonstrates that at 48 hr after infection of MDBK cells at 34.5° C. with IBRV(Los Angeles) and IBRV(NG)dltkdlgIII, respectively, the virus yields had increased to $7.7 \times 10^7$ and $2.1 \times 10^8$ p.f.u./ml (titrations at 34.5° C.). The 48 hr yields of the IBRV-(Los Angeles) and IBRV(NG)dltkdlgIII grown at 39.1° C., respectively, were about $3.9 \times 10^7$ and $5.1 \times 10^7$ (titrations at 34.5° C.). Within experimental error, the yields were similar for titrations performed at 39.1° C. and 34.5° C. Thus, it is clear that the recombinant virus, tk− IBRV(NG)dltkdlgIII can grow about as well over the temperature range of 34.5° C. to 39.1° C. as the wild-type IBRV(Los Angeles) strain. That is, neither virus exhibits temperature-sensitive properties. In this regard, tk− IBRV(NG)dltkdlgIII also resembles the tk− IBRV strains previously described, i.e., IBRV(B8-D53) and IBRV(NG)dltk (U.S. Pat. Nos. 4,569,840 and U.S. Pat. No. 4,703,011).

While the invention has been described in detail and with reference to specific embodiments thereof, it will be apparent to one skilled in the art that various changes and modifications can be made therein without departing from the spirit and scope thereof.

We claim:

1. A vaccine for infectious bovine rhinotracheitis disease comprising:
   (1) A pharmaceutially effective amount of an infectious bovine rhinotracheitis virus which fails to produce any antigenic IBRV gIII polypeptides as a result of a deletion, an insertion or both a deletion and an insertion in the IBRV gIII gene; and
   (2) A pharmaceutially acceptable carrier or diluent.

2. The vaccine for infectious bovine rhinotracheitis disease as claimed in claim 1, wherein said infectious bovine rhinotracheitis virus fails to produce any antigenic IBRV gIII polypeptides as a result of a deletion in the IBRV gIII gene.

3. The vaccine for infectious bovine rhinotracheitis disease as claimed in claim 2, wherein said deletion is about 10 to 1500 bp in size.

4. The vaccine for infectious bovine rhinotracheitis disease as claimed in claim 3, wherein said deletion is about 75 to 200 bp in size.

5. The vaccine for infectious bovine rhinotracheitis disease as claimed in claim 1, wherein said insertion is about 8 to 5000 bp in size.

6. The vaccine for infectious bovine rhinotracheitis disease as claimed in claim 1, wherein said infectious bovine rhinotracheitis virus also fails to produce any functional TK as a result of a mutation in the IBRV tk gene.

7. The vaccine for infectious bovine rhinotracheitis disease as claimed in claim 6, wherein said mutation in the IBRV tk gene is a deletion mutation.

8. The vaccine for infectious bovine rhinotracheitis disease as claimed in claim 1, wherein said infectious bovine rhinotracheitis virus is also temperature-resistant.

9. The vaccine for infectious bovine rhinotracheitis disease as claimed in claim 1, wherein said virus has the identifying characteristics of IBRV(NG)dltkdlgIII (ATCC No. VR-2181).

10. The vaccine for infectious bovine rhinotracheitis disease as claimed in claim 1, wherein said virus is lyophilized.

11. The vaccine for infectious bovine rhinotracheitis disease as claimed in claim 1, wherein said pharmaceutically acceptable carrier or diluent is physiologically buffered medium containing 2.5 to 15% serum which does not contain antibodies to infectious bovine rhinotracheitis virus.

12. The vaccine for infectious bovine rhinotracheitis disease as claimed in claim 11, wherein said serum is selected from the group consisting of swine serum, calf serum, fetal calf serum, horse serum and lamb serum.

13. The vaccine for infectious bovine rhinotracheitis disease as claimed in claim 1, wherein said pharmaceutically effective amount is $10^{4.5}$ to $10^{7.0}$ p.f.u.

14. The vaccine for infectious bovine rhinotracheitis disease as claimed in claim 13, wherein said pharmaceutically effective amount is $10^{4.5}$ to $10^{5.5}$ p.f.u.

15. A vaccine for infectious bovine rhinotracheitis disease comprising:
(1) a pharmaceutically effective amount of an infectious bovine rhinotracheitis virus which fails to produce any antigenic IBRV gIII polypeptides as a result of a deletion in the IBRV gIII gene produced by the process comprising:
(a) Constructing a hybrid plasmid comprising a cloning vector and a DNA fragment of IBRV containing substantially all of the IBRV gIII gene flanking sequences thereof;
(b) Deleting DNA sequences from the hybrid plasmid of step (a) such that less than substantially all of the IBRV gIII gene is present, while retaining IBRV DNA sequences adjacent to each side of the deletion;
(c) Co-transfecting, in IBRV host cells, the hybrid plasmid of step (b) with infectious gIII+ IBRV DNA; and
(d) Screening the progeny viruses obtained in step (c) so as to identify and produce IBRV mutants which fail to produce any antigenic IBRV gIII polypeptides as a result of a deletion in the IBRV gIII gene, and
(2) A pharmaceutically acceptable carrier or diluent.

16. The vaccine for infectious bovine rhinotracheitis disease as claimed in claim 15, wherein said deletion is about 10 to 1500 bp in size.

17. The vaccine for infectious bovine rhinotracheitis disease as claimed in claim 16, wherein said deletion is about 75 to 200 bp in size.

18. The vaccine for infectious bovine rhinotracheitis disease as claimed in claim 15, wherein the infectious gIII+ IBRV DNA of step (c) is derived from an IBRV mutant which fails to produce any functional TK such that the resulting IBRV mutants of step (d) fail to produce any antigenic IBRV gIII polypeptides as a result of a deletion in the IBRV gIII gene and fail to produce any functional TK as a result of a mutation in the IBRV tk gene.

19. The vaccine for infectious bovine rhinotracheitis disease as claimed in claim 18, wherein said IBRV mutant which fails to produce any functional TK, fails to produce such as a result of a deletion in the IBRV tk gene.

20. The vaccine for infectious bovine rhinotracheitis disease as claimed in claim 19, wherein said IBRV mutant is IBRV(NG)dltk.

21. The vaccine for infectious bovine rhinotracheitis disease as claimed in claim 15, wherein the infectious gIII+ IBRV DNA of step (c) is derived from a temperature-resistant IBRV such that the resulting IBRV mutants of step (c) are temperature-resistant IBRV mutants which fail to produce any antigenic IBRV gIII polypeptides as a result of a deletion in the IBRV gIII gene.

22. The vaccine for infectious bovine rhinotracheitis disease as claimed in claim 15, additionally comprising step (e):
(e) Propagating the resulting IBRV mutants of step (d) at a non-permissive temperature for a temperature-sensitive virus so as to select for and produce temperature-resistant IBRV mutants which fail to produce any antigenic IBRV gIII polypeptides as a result of a deletion in the IBRV gIII gene.

23. The vaccine for infectious bovine rhinotracheitis disease as claimed in claim 15, wherein said cloning vector is selected from the group consisting of pBR322, pBR325, pMB9, pKH47, pBR328, pHC79, pUC18, pUC19, phage Charon 28, pKB11, pKSV-10 and pMAR420.

24. The vaccine for infectious bovine rhinotracheitis disease as claimed in claim 23, wherein said cloning vector is pBR322.

25. The vaccine for infectious bovine rhinotracheitis disease as claimed in claim 15, wherein the resulting hybrid plasmid of step (b) is pLAHKdlApaI.

26. The vaccine for infectious bovine rhinotracheitis disease as claimed in claim 15, wherein said virus is lyophilized.

27. The vaccine for infectious bovine rhinotracheitis disease as claimed in claim 15, wherein said pharmaceutically acceptable carrier or diluent is physiologically buffered medium containing 2.5 to 15% serum which does not contain antibodies to infectious bovine rhinotracheitis virus.

28. The vaccine for infectious bovine rhinotracheitis disease as claimed in claim 27, wherein said serum is selected from the group consisting of swine serum, calf serum, fetal calf serum, horse serum and lamb serum.

29. The vaccine for infectious bovine rhinotracheitis disease as claimed in claim 15, wherein said pharmaceutically effective amount is $10^{4.5}$ to $10^{7.0}$ p.f.u.

30. The vaccine for infectious bovine rhinotracheitis disease as claimed in claim 29, wherein said pharmaceutically effective amount is $10^{4.5}$ to $10^{5.5}$ p.f.u.

31. The vaccine for infectious bovine rhinotracheitis disease as claimed in claim 15, wherein a foreign DNA sequence is inserted in place of the IBRV gIII gene sequences deleted in step (b) such that the IBRV DNA sequences adjacent to each side of the deleted IBRV gIII gene sequences are retained and such that the resulting IBRV mutants of step (d) fail to produce any antigenic IBRV gIII polypeptides as a result of both a deletion and insertion in the IBRV gIII gene.

32. The vaccine for infectious bovine rhinotracheitis disease as claimed in claim 31, wherein the foreign DNA sequence is about 8 to 5000 bp in size.

33. The vaccine for infectious bovine rhinotracheitis disease as claimed in claim 31, wherein the infectious gIII+ IBRV DNA of step (c) is derived from an IBRV mutant which fails to produce any functional TK such that the resulting IBRV mutants of step (d) fail to produce any antigenic IBRV gIII polypeptides as a result of both a deletion and insertion in the IBRV gIII gene and fail to produce any functional TK as a result of a mutation in the IBRV tk gene.

34. The vaccine for infectious bovine rhinotracheitis disease as claimed in claim 33, wherein said IBRV mutant which fails to produce any functional TK, fails to produce such as a result of a deletion in the IBRV tk gene.

35. The vaccine for infectious bovine rhinotracheitis disease as claimed in claim 34, wherein said IBRV mutant is IBRV(NG)dltk.

36. The vaccine for infectious bovine rhinotracheitis disease as claimed in claim 33, wherein the infectious gIII+ IBRV DNA of step (c) is derived from a temperature-resistant IBRV such that the resulting IBRV mutants of step (d) are temperature-resistant IBRV mutants which fail to produce any antigenic IBRV gIII polypeptides as a result of both a deletion and insertion in the IBRV gIII gene.

37. The vaccine for infectious bovine rhinotracheitis disease as claimed in claim 31, additionally comprising step (e):
(e) Propagating the resulting IBRV mutants of step (d) at a non-permissive temperature for a temperature-sensitive virus so as to select for and produce a temperature-resistant IBRV which fails to produce any antigenic IBRV gIII polypeptides as a result of both a gIII gene.

38. The vaccine for infectious bovine rhinotracheitis disease as claimed in claim 31, cloning vector is selected from the group consisting of pBR322, pBR325, pMB9, pKH47, pBR328, pHC79, pUC18, pUC19, phage Charon 28, pKB11, pKSV-10 and pMAR420.

39. The vaccine for infectious bovine rhinotracheitis disease as claimed in claim 38, wherein said cloning vector is pBR322.

40. The vaccine for infectious bovine rhinotracheitis disease as claimed in claim 31, wherein said virus is lyophilized.

41. The vaccine for infectious bovine rhinotracheitis disease as claimed in claim 31, wherein said pharmaceutically acceptable carrier or diluent is physiologically buffered medium containing 2.5 to 15% serum which does not contain antibodies to infectious bovine rhinotracheitis virus.

42. The vaccine for infectious bovine rhinotracheitis disease as claimed in claim 41, wherein said serum is selected from the group consisting of swine serum, calf serum, fetal calf serum, horse serum and lamb serum.

43. The vaccine for infectious bovine rhinotracheitis disease as claimed in claim 31, said pharmaceutically effective amount is $10^{4.5}$ to $10^{7.0}$ p.f.u.

44. The vaccine for infectious bovine rhinotracheitis disease as claimed in claim 43, wherein said pharmaceutically effective amount is to $10^{5.5}$ p.f.u.

45. A vaccine for infectious bovine rhinotracheitis disease comprising:
(1) a pharmaceutically effective amount of an infectious bovine rhinotracheitis virus which fails to produce any antigenic IBRV gIII polypeptides as a result of an insertion in the IBRV gIII gene produced by the process comprising:
    (a) Constructing a hybrid plasmid comprising a cloning vector and a DNA fragment of IBRV containing substantially all of the IBRV gIII gene and flanking sequences thereof;
    (b) Inserting a foreign DNA sequence into the hybrid plasmid of step (a) such that no antigenic IBRV gIII polypeptides are produced and such that IBRV DNA sequences adjacent to each side of the insertion are retained;
    (c) Co-transfecting, in IBRV host cells, the resulting hybrid plasmid of step (b) with infectious gIII+ IBRV DNA; and
    (d) Screening the progeny viruses obtained in step (c) so as to identify and produce IBRV mutants which fail to produce any antigenic IBRV gIII polypeptides as a result of an insertion in the IBRV gIII gene, and
(2) A pharmaceutically acceptable carrier or diluent.

46. The vaccine for infectious bovine rhinotracheitis disease as claimed in claim 45, wherein said insertion is about 8 to 5000 bp in size.

47. The vaccine for infectious bovine rhinotracheitis disease as claimed in claim 45, wherein the infectious DNA of step (c) is derived from an IBRV mutant which fails to produce any functional TK such that the resulting IBRV mutants of step (d) fail to produce any antigenic IBRV gIII polypeptides as a result of an insertion in the IBRV gIII gene and fail to produce any functional TK as a result of a mutation in the IBRV tk gene.

48. The vaccine for infectious bovine rhinotracheitis disease as claimed in claim 47, wherein said IBRV mutant which fails to produce any functional TK, fails to produce such as a result of deletion in the IBRV tk gene.

49. The vaccine for infectious bovine rhinotracheitis disease as claimed in claim 48, wherein said IBRV mutant is IBRV(NG)dltk.

50. The vaccine for infectious bovine rhinotracheitis disease as claimed in claim 45, wherein the infectious gIII+ IBRV DNA of step (c) is derived from a temperature-resistant IBRV such that the resulting IBRV mutants of step (d) are temperature-resistant IBRV mutants which fail to produce any antigenic IBRV gIII polypeptides as a result of an insertion in the IBRV gIII gene.

51. The vaccine for infectious bovine rhinotracheitis disease as claimed in claim 45, additionally comprising step (e): (e) Propagating the resulting IBRV of step (d) at a on-permissive temperature for a temperature-sensitive virus so as to select for and produce a temperature-resistant IBRV which fails to produce any antigenic IBRV gIII polypeptides as a result of an insertion in the IBRV gIII gene.

52. The vaccine for infectious bovine rhinotracheitis disease as claimed in claim 45, wherein said cloning vector is selected from the group consisting of pBR322, pBR325, pMB9, pKH47, pBR328, pHC79, pUC18, pUC19, phage Charon 28, pKB11, pKSV-10 and pMAR420.

53. The vaccine for infectious bovine rhinotracheitis disease as claimed in claim 52, wherein said cloning vector is pBR322.

54. The vaccine for infectious bovine rhinotracheitis disease as claimed in claim 45, wherein said virus is lyophilized.

55. The vaccine for infectious bovine rhinotracheitis disease as claimed in claim 45, wherein said pharmaceutically acceptable carrier or diluent is physiologically buffered medium containing 2.5 to 15% serum which does not contain antibodies to infectious bovine rhinotracheitis virus.

56. The vaccine for infectious bovine rhinotracheitis disease as claimed in claim 55, wherein said serum is selected from the group consisting of swine serum, calf serum, fetal calf serum, horse serum and lamb serum.

57. The vaccine for infectious bovine rhinotracheitis disease as claimed in claim 45, wherein said pharmaceutically effective amount is $10^{4.5}$ to $10^{7.0}$ p.f.u.

58. The vaccine for infectious bovine rhinotracheitis disease as claimed in claim 57, wherein said pharmaceutically effective amount is $10^{4.5}$ to $10^{5.5}$ p.f.u.

* * * * *

UNITED STATES PATENT AND TRADEMARK OFFICE
CERTIFICATE OF CORRECTION

PATENT NO. : 5,128,129
DATED : July 7, 1992
INVENTOR(S) : Malon Kit, Saul Kit, Haruki Otsuka It is certified that error appears in the above-indentified patent and that said Letters Patent is hereby corrected as shown below:

In column 1, line 13, after "Human Services", insert --The Government has certain reights --.

Signed and Sealed this

Twenty-fifth Day of April, 1995

Attest:

BRUCE LEHMAN

Attesting Officer     Commissioner of Patents and Trademarks